US00RE40667E

(19) United States
(12) Reissued Patent
Roth

(10) Patent Number: US RE40,667 E
(45) Date of Reissued Patent: Mar. 17, 2009

(54) **[R-(R*R*)]-2-(4-FLUOROPHENYL)-β,δ-DIHYDROXY-5-(1-METHYLETHYL-3-PHENYL-4-[(PHENYLAMINO)CARBONYL]-1H-PYRROLE-1-HEPTANOIC ACID, ITS LACTONE FORM AND SALTS THEREOF**

(75) Inventor: Bruce Roth, San Jose, CA (US)

(73) Assignee: Warner-Lambert Company LLC, New York, NY (US)

(21) Appl. No.: 11/653,830

(22) Filed: Jan. 16, 2007

Related U.S. Patent Documents

Reissue of:
(64) Patent No.: 5,273,995
Issued: Dec. 28, 1993
Appl. No.: 07/660,976
Filed: Feb. 26, 1991

U.S. Applications:
(

(63) Continuation of application No. 07/384,187, filed on Jul. 21, 1989, now abandoned.

(51) Int. Cl.
*A61K 31/40* (2006.01)
*A61K 31/35* (2006.01)
*C07D 207/327* (2006.01)

(52) U.S. Cl. ..... 514/422; 514/423; 548/517; 548/537

(58) Field of Classification Search ..... 514/422, 514/423; 548/517, 537
See application file for complete search history.

(56) References Cited

U.S. PATENT DOCUMENTS

| | | | |
|---|---|---|---|
| 3,808,254 | A | 4/1974 | Matthews |
| 3,965,129 | A | 6/1976 | Perry et al. |
| 3,983,140 | A | 9/1976 | Endo et al. |
| 4,072,698 | A | 2/1978 | Hylton et al. |
| 4,137,322 | A | 1/1979 | Endo et al. |
| 4,139,555 | A | 2/1979 | Zerbes |
| 4,171,359 | A | 10/1979 | Weinstock |
| 4,192,872 | A | 3/1980 | Weinstock |
| 4,231,938 | A | 11/1980 | Monaghan et al. |
| 4,281,132 | A | 7/1981 | Ward |
| 4,282,155 | A | 8/1981 | Smith et al. |
| 4,293,496 | A | 10/1981 | Willard |
| 4,319,039 | A | 3/1982 | Albers-Schonberg |
| 4,342,761 | A | 8/1982 | Ward |
| 4,342,767 | A | 8/1982 | Albers-Schonberg et al. |
| 4,346,227 | A | 8/1982 | Terahara et al. |
| 4,374,829 | A | 2/1983 | Harris et al. |
| 4,374,844 | A | 2/1983 | McCombie |
| 4,375,475 | A | 3/1983 | Willard et al. |
| 4,444,784 | A | 4/1984 | Hoffman et al. |
| 4,450,171 | A | 5/1984 | Hoffman et al. |
| 4,474,971 | A | 10/1984 | Wareing |
| 4,495,103 | A | 1/1985 | Terashima et al. |
| 4,555,511 | A | 11/1985 | Schnorrenberg et al. |

(Continued)

FOREIGN PATENT DOCUMENTS

| | | | |
|---|---|---|---|
| AU | 601981 | | 9/1990 |
| AU | 621874 | | 3/1992 |
| CA | 1161380 | | 1/1984 |
| CA | 1268768 | | 5/1990 |
| CA | 1304080 | | 6/1992 |
| CA | 1330441 | | 6/1994 |
| CA | 2021546 | | 4/1997 |
| CA | 2465565 | | 12/2004 |
| DK | 01 171 588 | | 12/1987 |
| DK | 171588 | B1 | 2/1997 |
| EP | 0 024 348 | | 3/1981 |
| EP | 0 114 027 | A1 | 7/1984 |
| EP | 0 171 588 | A1 | 2/1986 |
| EP | 0 211 416 | | 2/1987 |
| EP | 0 221 025 | A1 | 5/1987 |
| EP | 0 232 997 | | 8/1987 |
| EP | 0 247 633 | | 12/1987 |
| EP | 0 251 625 | | 1/1988 |
| EP | 0 259 086 | | 3/1988 |
| EP | 0 319 856 | A2 | 6/1989 |
| EP | 0 330 172 | | 8/1989 |
| EP | 89103078.5 | | 8/1989 |
| EP | 0 409 281 | | 1/1991 |
| IE | 1197/87 | L | 11/1987 |
| IE | 890391 | | 8/1989 |
| JP | 2240/1982 | | 1/1982 |
| JP | 10572/1983 | | 1/1983 |
| JP | 62-289577 | | 12/1987 |
| JP | 72652/1988 | | 4/1988 |
| KR | 1987-5372 | | 2/1994 |
| WO | WO 84/02131 | | 6/1984 |
| WO | PT84975 | | 6/1987 |
| WO | WO 88/07582 | | 10/1988 |
| WO | WO 89/07598 | | 8/1989 |
| WO | PT89774 | | 10/1989 |
| WO | WO 90/00553 | | 1/1990 |
| WO | WO 97 03959 | | 2/1997 |
| WO | WO 99/47138 | | 9/1999 |

OTHER PUBLICATIONS

Hall and Roush, *J. Org. Chem.*, 47: 4611–4621 (1982).
Roush and Gillis, *J. Org. Chem.*, 47: 4825–4829 (1982).
Sit et al, *J. Med. Chem.*, 33:2982 (1990).
Amin et al., *J. Pharmacology* 46:13 (1993).
Underberg et al., *J. Pharm. Biomed Anal.* 8(8–12): 681–683 (1990).
Stinson, *Chemical and Engineering News*, 70(39): 46–79 (1992).
Stinson, *Chemical and Engineering News*, 71(39): 38–64 (1993).

(Continued)

*Primary Examiner*—Joseph K. McKane
*Assistant Examiner*—Joseph R Kosack
(74) *Attorney, Agent, or Firm*—Connolly, Bove Lodge & Hutz LLP

(57) ABSTRACT

[R-(R*,R*)]-2-(4-fluorophenyl)-β,δ-dihydroxy-5-((1-methylethyl)-3-phenyl-4-[(phenylamino)-carbonyl)]-1H-pyrrole-1-heptanoic acid or (2R-trans)-5-(4-fluoro-phenyl)-2-(1-methylethyl-N,4-diphenyl-1-[2-(tetrahydro-4-hydroxy-6-oxo-2H-pyran-2-yl)ethyl]-1H-pyrrole-3-carboxamide; and pharmaceutically acceptable salts thereof.

3 Claims, No Drawings

U.S. PATENT DOCUMENTS

| | | | | | |
|---|---|---|---|---|---|
| 4,611,067 | A | | 9/1986 | Volante et al. | |
| 4,613,610 | A | | 9/1986 | Wareing | |
| 4,647,576 | A | | 3/1987 | Hoefle et al. | |
| 4,681,893 | A | | 7/1987 | Roth | |
| 4,697,036 | A | | 9/1987 | Giordano et al. | |
| 4,735,958 | A | | 4/1988 | Roth et al. | |
| 4,739,073 | A | | 4/1988 | Kathawala | |
| 4,743,450 | A | | 5/1988 | Harris et al. | |
| 4,775,681 | A | | 10/1988 | Heifetz | |
| 4,786,505 | A | | 11/1988 | Lovgren et al. | |
| 4,804,679 | A | | 2/1989 | Anderson | |
| 4,847,306 | A | | 7/1989 | Lee et al. | |
| 4,851,427 | A | | 7/1989 | Wareing | |
| 4,853,230 | A | | 8/1989 | Lovgren et al. | |
| 4,864,038 | A | | 9/1989 | Hoffman et al. | |
| 4,866,090 | A | | 9/1989 | Hoffman et al. | |
| 4,870,187 | A | | 9/1989 | Sit et al. | |
| 4,897,490 | A | | 1/1990 | Sit et al. | |
| 4,898,868 | A | | 2/1990 | Bergmann et al. | |
| 4,898,949 | A | | 2/1990 | Wright et al. | |
| 4,906,624 | A | | 3/1990 | Chucholowski et al. | |
| 4,939,159 | A | | 7/1990 | Anderson et al. | |
| 4,940,727 | A | | 7/1990 | Inamine et al. | |
| 4,950,775 | A | | 8/1990 | Heathcock et al. | |
| 4,962,115 | A | | 10/1990 | Van Daele | |
| 4,963,538 | A | | 10/1990 | Duggan et al. | |
| 4,968,689 | A | | 11/1990 | Angerbauer et al. | |
| 4,976,949 | A | | 12/1990 | Meyer et al. | |
| 4,978,791 | A | | 12/1990 | Völker et al. | |
| 4,992,462 | A | | 2/1991 | Hubsch et al. | |
| 5,001,255 | A | | 3/1991 | Kathawala et al. | |
| 5,003,080 | A | | 3/1991 | Butler et al. | |
| 5,004,651 | A | | 4/1991 | Becker | |
| 5,006,530 | A | | 4/1991 | Angerbauer et al. | |
| 5,024,999 | A | | 6/1991 | Fujikawa et al. | |
| 5,026,708 | A | | 6/1991 | Fujikawa et al. | |
| 5,030,447 | A | | 7/1991 | Joshi et al. | |
| 5,045,321 | A | | 9/1991 | Makino et al. | |
| 5,055,484 | A | | 10/1991 | Jendralla et al. | |
| 5,061,722 | A | | 10/1991 | Teetz et al. | |
| 5,093,132 | A | | 3/1992 | Makino et al. | |
| 5,097,045 | A | | 3/1992 | Butler et al. | |
| 5,124,482 | A | | 6/1992 | Butler et al. | |
| 5,149,837 | A | | 9/1992 | Butler et al. | |
| 5,151,433 | A | | 9/1992 | Fulbreth et al. | |
| 5,208,258 | A | | 5/1993 | Heathcock et al. | |
| 5,216,174 | A | | 6/1993 | Butler et al. | |
| 5,245,047 | A | | 9/1993 | Butler et al. | |
| 5,273,995 | A | | 12/1993 | Roth | |
| 5,280,126 | A | | 1/1994 | Butler et al. | |
| 5,354,772 | A | | 10/1994 | Kathawala | |
| 5,378,729 | A | | 1/1995 | Kohn et al. | |
| 5,969,156 | A | * | 10/1999 | Briggs et al. | 548/537 |
| 6,087,511 | A | | 7/2000 | Lin et al. | |
| 6,121,461 | A | | 9/2000 | McKenzie et al. | |
| 6,274,740 | B1 | | 8/2001 | Lin et al. | |
| 6,605,729 | B1 | | 8/2003 | Byrn et al. | |
| 7,144,915 | B2 | * | 12/2006 | Byrn et al. | 514/423 |
| 2006/0241169 | A1 | * | 10/2006 | Park | 514/423 |

OTHER PUBLICATIONS

Burlinson, *Tablets and Tabletting*, William Heinemann medical Books Ltd. : London, 1968.

Casy, A.F. Stereochemistry and Biological Activity. *Medicinal Chemistry*, Wiley: New York, 1970.

Rawlins, *Bentley's Textbook of Pharmaceutics*, 8th Ed., Bailliere Tindall: London, 1977.

Seeman, P. Drug Receptors. Kalant H. et al. eds., *Principles of Medical Pharmacology*, 4thEdition, University of Toronto Press: Toronto, 1985.

Lachman et al., Proformulation, *The Theory and Practice of Industrial Pharmacy*, 3rd Edition, Lea & Febiger: Philadelphia, 1986.

Lieberman et al., eds. *Pharmaceutical Dosage Forms Tablets*, 2nd Edition (vol. 1), Marcel Dekker: New York, 1989.

Gennaro, *Remington's Pharmaceutical Sciences*, 18th Ed., Mack Printing Company: Easton, Pennsylvania, 1990.

Banker, Rhodes, eds., *Modern Pharmaceutics*, 3rd Edition, Marcel Dekker, Inc.: New York, 1996.

Kibbe, A.H., ed., *Handbook of Pharmaceutical Excipients*, 3rd Ed., Pharmaceutical Press: London, 2000.

The Merck Index, 10th Edition (1983), entry 5949: *N–Methylglucamine*, pp. 870–871.

The Merck Index, 12th Edition (1996), entry 897: *Atorvastatin*, p. 146.

Transcript of evidence given by Dr. Scallen in *US trial of Prizer, Inc., et al.* v *Ranbaxy Laboratories Limited wt. al.*, Court file No. 03–209–JJF, on Dec. 3, 2004.

Guideline for Submitting Supporting Documentation in Drug Applications for the Manufacture of Drug Substances, Feb. 1987.

Stein et al., The Lovastatin–Niacin Trial: Effects on Lipoproteins. *Arteriosclerosis and Thrombosis* 11: 1458a (1991).

Dujovne et al., The Lovastatin–Niacin Trial: Adverse Events. *Arteriosclerosis and Thrombosis* 11: 1458a (1991).

Frost, P.H. et al., Lipid Metabolism. In PA Fitzgerald, Ed., *Handbook of Clinical Endocrinology*, 2nd Edition, Appleton and Lange, 1991.

Frost, P.H. et al., Lovastatin–Niacin Comparative Trial. *JACC* 19, 374A, 1992.

Lovastatin Study Groups I through IV. Lovastatin 5–year safety and efficacy study. *Arch. Intren. Med.* 153: 1079–1087 (1993).

Illingworth, D.R. et al., Comparative effects of lovastatin and niacin in primary hypercholesterolemia: A prospective trial. *Arch. Intern. Med.* 154: 1586–1595 (1994).

Stein, E.A. et al., Efficacy and tolerability of low–dose simvastatin and niacin, alone and in combination, in patients with combined hyperlipidemia: a prospective trial. J. *Cardiovasc. Pharmacol. Therapeut.* 1: 107–116 (1996).

Frost, P.H. et al., Rationale for use of non–high–density lipoprotein cholestrol rather than low–density lipoprotein cholesterol as a tool for lipoprotein cholestrol screening and assessment of risk and therapy, *Am. J. Cardiol.* 81: 26B–31B (1998).

Havel, R.J. et al., The role of non–high–density lipoprotein cholesterol in evaluation and treatment of lipid disorders. *J. Clin. Endocrinology and Metabolism* 85: 2105–2108 (2000).

The Cholestrol Myth, *Atlantic Monthly*, Sep. 1989.

National Cholesterol Education Program Guideline III (2004 Update).

Results of the National Cholesterol Education (NCEP) Program Evaluation Project Utilizing Novel E–Technology (NEPTUNE) II Survey and Implications for Treatment under Recent NCEP Writing Group Recommendations.

Chapter 1—Selling to Everyone High Cholesterol. In Moynihan R. and Cassels A., *Selling Sickness*, Avalon Publishing Group: 2005, pp. 1–21.

Letter dated Dec. 2, 2005 from Taylor Wessing to L. Caswell attaching expert reports of Dr. Newton dated May 27, 2005 and Jun. 17, 2005 that were filed in *Ranbaxy (UK)* v. *Warner–Lambert Company*, HC–04C 02167, and said reports.

Trial transcripts taken on Jul. 18 to 22, 2005 and Jul. 25, 2005 in *Ranbaxy (UK) Limited* v. *Warner–Lambert Company*, HC–04C 02167.

Warner–Lambert Company Notices of Application court files T–507–05, T–1128–05.

English translation of Austrian decisions invalidating Austrian Patent No. 207 ,896.

Lipitor advertising placed in the Canadian Medical Association Journal, from 1997 to 2005.

Consenus Conference. Lowering Blood Cholesterol to Prevent Heart Disease. *JAMA* 253: 1080–2086 (1985).

Report on the National Cholesterol Education Program Expert Panel on Detection, Evaluation, and Treatment of High Blood Cholesterol in Adults. The Expert Panel. *Arch. Intern. Med.* 148: 36–69 (1988).

Canadian Consenus Conference on Cholestrol. Final Report, Canadian Consenus Conference on the Prevention of Heart and Vascular Disease by Altering Serum Cholesterol and Serum Lipoprotein Factors. *CMAJ* 139: 111–63 (1988).

Frolich et al., Rationale for and Outline of the Recommendations of the Working Group of Hypercholesterolemia and Other Dyslipidemias: Interim Report. *Can. J. Cardiol.* 14 (supp. A): 17A–21A (1998).

Fodor et al., for the Working Group on Hypercholesterolemia and Other Dyslipidemias: Recommendations for the Management and Treatment of Dyslipidemia. CMAJ 162 (10): 1441–1447 (2000).

Fodor et al., Recommendations for the management of dyslipidemia and the prevention of cardiovascular disease: 2003 update. *CMAJ* 168(9): 921–924 (2003).

NHLBI News Release May 15, 2001, http://www.nhlbi.nih.gov/new/press/01–05–15.htm.

Manuel et al., The 2003 Canadian Recommendations for Dyslipidemia Management: Revisions are Needed. *CMAJ* 172: 1027–1032 (2005).

Documents compiled by the World Health Organization's Department of Essential Drugs & Medicines Policy published as http://www.drugpromo.info/read–reviews.asp?id=4 and http://www.drugpromo.info/read–reviews.asp?id=5.

Wazana, A., *JAMA* 283(3): (373–380 (2000).

Brophy et al., Statin wars following coronary revascularization—Evidence based clinical practice? *Can. J. Cardiol.* 22(1): 54–58 (2006).

Havel et al., A multicenter study of mevinolin (lovastatin) in treatment of heterozygous familial hypercholestolemia. *Annals Int. Med.* 107: 609 (1987).

Lovastatin Study Group III. A multicenter comparison of lovastatin and cholestyramine in the therapy of severe primary hypercholesterolemia. *JAMA* 260: 359 (1988).

Defendants' Trial Exhibit 3323, "Data Provided to Patent Office in '995 Specification and Data from Experiment 107," from *Pfizer, Inc et al.* v. *Ranbaxy Laboratories Limited et al.*, US District Court, District of Deleware, 03–209–JJF.

Defendants' Trial Exhibit 3325 from *Pfizer, Inc.* v. *Ranbaxy Laboratories Limited, et al.*, US District Court, District of Delaware, 03–209–JJF.

Defendants' Trial Exhibit 3325A from *Pflizer, Inc et al.* v. *Ranbaxy Laboratories Limited, et al.*, US District Court, District of Delaware, 03–209–JJF.

Dietschy 1, CSI $IC_{50}$ values, from *Pfizer, Inc et al.* v. *Ranbaxy Laboratories Limited, et al.*, US District Court, District of Delaware, 03–209–JJF.

Dietschy 2, COR $IC_{50}$ values, from *Pfizer, Inc et al.* v. *Ranbaxy Laboratories Limited, et al.*, US District Court, District of Delaware, 03–209–JJF.

Dietschy 3, $IC_{50}$ values (nM) for head–to–head CSI and COR screens, from *Pfizer, Inc et al.* v. *Ranbaxy Laboratories Limited, et al.*, US District Court, District of Delaware, 03–209–JJF.

Dietschy 4, AICS data, from *Pfizer, Inc et al.* v. *Ranbaxy Laboratories Limited.* et al., US District Court, District of Delaware, 03–209–JJF.

Defendants' Trial Exhibit 319 from *Pfizer, Inc et al.* v. *Ranbaxy Laboratories Limited, et al.*, US. District Court, District of Delaware, 03–209–JJF.

Defendants' Trial Exhibit 321 from *Pfizer, Inc et al,* v. *Ranbaxy Laboratories Limited, et al.*, US District Court, District of Delaware, 03–209–JJF.

Roth et al., Inhibitors of cholesterol biosynthesis. 3. Tetrahydro–4–hydroxy–6–[2–1H–pyrrol–1–yl)ethyl]–2H–pyran–2–one inhibitors of HMG–CoA reductase. 2. Effects of introducing substituents at positions three and four of the pyrrole nucleus. *J. Med. Chem.* 34(1): 357–366 (Jan. 1991).

Warner–Lambert Pharmaceutical Research Report No. RR–740–02620, Acute Inhibition of Cholesterol Synthesis in the Rat by the Calcium Salts (Racemic and Chiral) of CI–971, dated May 31, 1989, identified as DTX 11 in *Pfizer, Inc et al.* v. *Ranbaxy Laboratories Limited, et al.*, US District Court, District of Delaware, 03–209–JJF.

Warner–Lambert/Parke–Davis memo to Oberkfell and Pieroni from Newton and Roth re: PD 134298–38A Product Profile A for HMG–Co–A Reductase Inhibitor, Jun. 1, 1989, identified as DTX 142 in *Pfizer, Inc et al.* v. *Ranbaxy Laboratories Limited, et al.*, US District Court, District of Delaware, 03–209–JJF.

Warner–Lambert/Parke–Davis Pharmaceutical Research Report RR–740–01682, CSI (Cholesterol Synthesis Inhibitors): A Rapid Screen for Inhibitors of Cholesterol Synthesis in Crude Microsomal Preparations from Rat Liver, dated May 3, 1985, identified as DTX 271 in *Pfizer, Inc et al.* v. *Ranbaxy Laboratories Limited, et al.*, US District Court, District of Delaware, 03–209–JJF.

Parke–Davis Memo re: Lead Compound Pharmacological Profile for CI–981 (PD 134298–38A) to Mr. H.F. Oberkfell and Mr. J. Peroni from Newton and Roth, dated Sep. 28, 1989, identified as DTX 4 in *Pfizer, Inc et al.* v. *Ranbaxy Laboratories Limited, et al.*, US District Court, District of Delaware, 03–209–JJF.

Chemist's Binder of Biological Data, identified as DTX 552, in *Pfizer, Inc et al.,* v. *Ranbaxy Laboratories Limited, et al.*, US District Court, District of Delaware, 03–209–JJF.

CI–981 IND submitted to the FDA, identified as DTX 326 in *Pfizer, Inc et al.* v. *Ranbaxy Laboratories Limited, et al.*, US District Court, District of Delaware, 03–209–JJF.

Sit et al., Synthesis, Biological Profile, and Quantitative Structure Activity Relationship of a Series of Novel 3–Hydroxy–3–methylglutaryl Coenzyme A Reductase Inhibitors. *J. Med. Chem.*33: 2982–2999 (1990).

Alberts Am.J.Cardiology vol. 62, 10J–15J (1988).

Alberts Proc Natl Acad Sci USA Jul. 1980;777(7):3957–61.

Ariëns et al. Cholinergic and Anticholinergic Drugs: Do they act on common receptors?, Ann NY Acad Sci, vol. 144, pp. 842–868 (1967).
Ariëns Stereochemistry and Biological Activity of Drugs, 11–53, 89–102, 161–185 (1983).
Ariëns Stereochemistry, a Basis for Sophisticated Nonsense in Pharmacokinetics and Clinical Pharmacology, Eur. J. Clin. Pharmacol., vol. 26, pp. 663–668 (1984).
Ariëns, E.J. "Implications of the Neglect of Stereochemistry in Pharmacokinetics and Clinical Pharmacology", Drug Intelligence and Clinical Pharmacy, (Oct. 1987), vol. 21, 827–829.
Ariëns, E.J., "Stereochemistry in the Analysis of Drug–Action. Part II", Medicinal Research Reviews, (1987), vol. 7, No. 3, 367–387.
Ariëns, E.J., "Stereochemistry: A Source of Problems in Medicinal Chemistry", Medicinal Research Reviews, (1986), vol. 6, No. 4, 451–466.
Ariëns, Chirality in bioactive agents and its pitfalls, TIPS, Elsevier Science Publishers B.V., Amsterdam, pp. 200–205 (1986).
Audebert Direct Resolution of Enantiomers in Column Liquid Chromatography, J. Liquid Chromatography, vol. 2, No. 8, 1063–1095 (1979).
Banitt, E.H. et al., "Resolution of Flecainide Acetate, N–(2–Piperidylmethyl)–2,5–bi5(2,2,2,–trifluoroethoxy) benzamide Acetate, and Antiarrhythmic Properties of the Enantiomers", J. Med. Chem. (1986),29:299–302.
Berge et al. Pharmaceutical Salts, J. Pharm. Sci., vol. 66(1):1–19 (1977).
Braun, M et al., Tetrahedron Lett., 25, 5031–5034 (1984).
Brown, A.G. et al., "Crystal and Molecular Structure of Compactin, a New Antifungal Metabolite from *Penicillium brevicompactum*", J. Chem. Soc. Perkin I, (1976) 1165–1170.
Burger Medicinal Chemistry, Chapter 7, pp. 81–107 (1970).
Carey et al. "Advanced Organic Chemistry", 2nd Ed., Chapter 2 and p. 75 (1984).
Stinson Chemical and Engineering News, 70, Sep. 28, 46 (1992).
Stinson Chemical and Engineering News, 71, Sep. 27, 38 (1993).
Collet et al. Optical Resolution by Direct Crystallization of Enantiomer Mixtures, Chemical Reviews, vol. 80, No. 3, 215–230 (1980).
Conant et al. The Chemistry of Organic Compounds, A Year's Course in Organic Chemistry, $4^{th}$ ed. Macmillan, New York, 1954, p. 234.
Cook Enantioselective Drug Analysis, Pharmacy International, vol. 6, No. 12, pp. 302–305 (1985).
Decamp Chirality, 1989, 1:2–6.
Demerson et al. Resolution of Etodolac and Antiinflammatory and Prostaglandin Synthetase inhibiting Properties of the Enantiomers, J. Med. Chem., vol. 26, No. 12, 1778–1780 (1983).
Dotsevi, C. et al., "Chromatographic Optical Resolution through Chiral Complexation of Amino Ester Salts by a Host Covalently Bound to Silica Gel", J. Am. Chem. Soc., (1975), 97:1259–1261.
Dugan, R.E. et al., "Factors Affecting the Diurnal Variation in the Level of β–Hydroxy–β–Methylglutaryl Coenzyme A Reductase and Cholestrol–Synthesizing Activity in Rat Liver", Archiv. Biochem. Biophys., (1972), 152:21–27.
Eliel et al., Stereochemistry of Organic Compounds, Wiley, New York, 1994, pp. 329–331, and remainder of Section 7–3.
Eliel et al., Section 3–1—Compounds with One Asymmetric Carbon Atom, Stereochemistry of Carbon Compounds, McGraw–Hill Book Company, Inc. (1962).
Eliel et al., Section 4–4—Resolution of Racemic Modifications, Stereochemistry of Carbon Compounds, McGraw–Hill Book Company, Inc. pp. 47–74 (1962).
Endo, J Med Chem., 28: 401–405 (1985).
Endo, A. et al., "Biochemical Aspect of HMG CoA Reductase Inhibitors", Adv. in Enzyme Regulation, Proceedings of the 28 Symposium on Regulation of Enzyme Activity and Synthesis in Normal and Neoplastic Tissues held at Indiana University School of Medicine, Indianapolis, Indiana, (Oct. 2 and 3, 1988), vol. 28, pp. 53–64.
Endo, A. et al., "Inhibition of Cholesterol Synthesis in vitro and in vivo by ML–236A and ML–236B, Competitive Inhibitors of 3–Hydroxy–3–methylglutaryl– Coenzyme A Reductase", Eur. J. Biochem., (1977), 77:31–36.
Endo, A., "Chemistry, Biochemistry, and Pharmacology of HMG–CoA Reductase Inhibitors," Klin. Wochenschr, (1988) 66:421–427.
Falck, J.R. et al., "Total Synthesis of (+)–Dihydromevinolin", Tetrahedron Letters, (1984), vol. 25, No. 33, pp. 3563–3566.
Fessenden et al. Section 4.10—Resolution of a Racemic Mixture, Organic Chemistry, $2^{nd}$ Ed., Willard Grant Press, Boston (1982).
Fieser et al. Organic Chemistry, D. C. Heath, Boston, 2nd ed., 1950, pp. 267–274.
Fogassy, E. et al., "Pseudosymmetry and Chiral Discrimination in Optical Resolution via Diasteroisomeric Salt Formation. The Crystal Structures of (R)– and (S)–N–Methylamphetamine Bitartrates (RMERTA and SMERTA)", J. Chem. Soc. Perkin Trans. II, (1986) 1881–1886.
Gekkan–Yakuji, vol. 29, No. 10, pp. 23–26 ( with English translation).
Goldman, M. et al., "Resolution of Chiral Olefinic Hydrocarbons and Sulfoxides by High–Performance Liquid Chromatography via Diasteromeric Platinum Complexes", J. Am. Chem. Soc.; (1982) 104:1093–1095.
Gould, P.L., "Salt Section for Basic Drugs", Int. J. Pharmaceutics, (1986), 33.201–217.
Greene Chapter 6—Preformulation, in Modem Pharmaceutics, Banker and Rhodes, Marcel Dekker Inc., New York.
Grieco, P.A. et al., "Convergent, Enantiospecific Total Synthesis of the Hypocholesterolemic Agent (+)– Compactin", J. Am. Chem. Soc., (1986) 108:5908–5919.
Grieco, P.A. et al., "Total Synthesis of the Hypocholesterolemic Agent (+)– Compactin", J. Am.Chem. Soc., (1983), 105:1403–1404.
Grundy, S.M., "HMG–CoA Reductase Inhibitors for Treatment of Hypercholesterolemia", N.E. J. Med., (Jul. 7, 1988), vol. 319, No. 1, pp. 24–33.
Guindon, Y. et al., "Preparation of ethyl 5(S),6–epoxy–3(R)–(methoxymethoxy)hexanoate: A key chiral intermediate for mevinolin and compactin", Tetrahedron Letters, (1985), vol. 26, No. 9, pp. 1185–1188.
Heathcock et al. J. Med. Chem. 1987, 30, 1858–1873.
Heathcock et al. J. Med. Chem. 1989, 32, 197–202.
Helmchen et al, Agnew Chem. Int. Edn. 1979. 18, pp. 63–65.
Hirama M. et al., "Chiral Total Synthesis of Compactin", J. Am. Chem. Soc., (1982), 104:4251–4253.

Hirama, M. et al., "Total Synthesis of (+)–Monacolin K (Mevinolin)", Tetrahedron Letters, (1983), vol. 24, No. 17, pp. 1811–1812.
Hoeg, J.M. et al., "3.–Hydroxy–3–Methylglutaryl–Coenzyme A Reductase Inhibitors in the Treatment of Hypercholesterolemia", JAMA, (Dec. 25, 1987), vol. 258, No. 24, p. 3532–3536.
Hoffman et al, J. Med. Chem., 29: 159–169 (Feb. 1986).
Hoffman W.F. et al., "3–hydroxy–3–methylglutaryl–coenzyme A reductase inhibitors. 4. Side Chain Ester Derivatives of Mevinolin", J. Med. Chem. (1986) 29:849–852.
Hsu, C–T, et al., "Total Synthesis of the Hypocholesterolemic Agent Compactin", J. Am. Chem.Soc., (1983), 105:593–601.
Hubbard et al. Chiral Pharmacology and its Consequences for Therapeutic Monitoring, Clin. Biochem., vol. 19, pp. 107–112 (1986).
Jackson et al. Characterization and Antifertility Activity in Rats of S(+) a–Chlorohydrin Chem.–Biol Interactions, vol. 17, No. 1, 117–120 (1977).
Jacques et al Enantiomers, Racemates, and Resolutions, John Wiley & Sons, Toronto (1981)(See C–56–59 for mention of specific sections).
Jacques et al. Types of Crystalline Racemates, Enantiomers, Racemates, and Resolutions, c.1, 3–23 (1981).
Jacques et al. Formation and Seperation of Diastereomers, Enantiomers, Racemates, and Resolutions, c.5, 251–281 (1981).
Jacques et al Section 5.1.2—Resolution of Bases, Enantiomers, Racemates, and Resolutions, John Wiley & Sons, Toronto (1981).
Jacques et al. Experimental Aspects and Art of Resolutions, Enantiomers, Racemates, and Resolutions, c.7, 378–434 (1981).
Johnson et al. Tetrahedron Letters, vol. 29, No. 31, pp. 3757–3760, 1988.
Kalant et al Chapter 9—Drug Receptors, Principles of Medical Pharmacology, 4th ed., University of Toronto Press, Toronto (1985).
Kalant et al Chapter 10—Specificity of Drug Action, Principles of Medical Pharmacology, 4th ed., University of Toronto Press, Toronto (1985).
Kaneko et al. Eur. J. Biochem., 87:313–321 (1978).
Kathawala, E.G., "Exciting Developments in the Area of HMG–CoA Reductase Inhibitors", Trends in Medicinal Chemistry '88: Proceedings of the Xth International Symposium on Medicinal Chemistry, Budapest, Aug. 15–19, 1988, (disclosed at the conference in Aug. 1988), pp. 709–728 (textbook received at CISTI on Jun. 23, 1989).
Kemp et al. Organic Chemistry, Worth, New York, 1980, pp. 172 and 173.
Kim, Y.H. et al., Chiral Differentiation by the P–(+)– Hexahelicene–7,7'–dicarboxylic Acid Disodium Salt. Resolution of N–2,4–Dinitrophenyl–α–amino–acid Esters by High Performance Liquid Chromatography, J. Chem. Soc., Chem. Commun., (1982), p. 1336–1337.
Krause et al. Atherosclerosis, 117:237 (1995).
Lee, TIPS, 8:442–446 (1987).
Lee, T–J, "An expeditious chiral route to analogs of mevinolin and compactin", Tetrahedron Letters, (1985), vol. 26, No. 41, pp. 4995–4996.
Lee, T–J, et al., "Structural Modification of Mevinolin", J. Org. Chem., (1982), 47:4750–4757.
Lehmann et al. Stereoselectivity and Affinity in Molecular Pharmacology, Jucker, E.(ed), Progress in Drug Research, vol. 20, Birkhauser, Basel Stuttgard, pp. 101–142.
Lehmann Stereoselective Molecular Recognition in Biology. Cuatrecasas, P., Greaves M.F. (eds), Receptors and Recognition, vol. 5, Series A, Chapman and Hall, London, pp. 1–77 (1978).
Lim et al. Enantiomeric resolution of di–threo–methylphenidate, U.S.P. (Ritalin®), by high– performance liquid chromatography, J. Chromatology, vol. 328, 378–386 (1985).
Liu et al. Effect of Enantiomeric Purity on Solubility Determination of Dexclamol Hydrochloride, J. Pharm. Sci., vol. 67, pp. 636–638 (1978).
Lynch et al., Tetrahedron Letters, 28: 1385–1388 (1987).
Majewski et al. Tetrahedron Letters, vol. 25, No. 20 pp. 2101–2104 1984.
Mantell, G., "Lipid Lowering Drugs in Atherosclerosis—The HMG–CoA Reductase Inhibitors", Clin. and Exper. Hyper.–Theory and Practice, (Jan. 1, 1989), vol. 11, Issue 5–6, 927–941.
March Methods of Resolution, in Advanced Organic Chemistry—Reactions, Mechanisms and Structure, 2nd Ed., McGraw Hill, New York 1977, pp. 108–111.
Martindale, The Extra Pharmacopoeia (ed. Reynolds 28th ed. 1982), p. 44.
McBlain et al. Facile Route to the Resolution of the Enantiomers of 1–Chloro–2–[2,2,2,–trichloro–1–(4–chlorophenyl) ethyl]benzene (o.p'–DDT), J. Ag. Food Chem., vol. 25, No. 1, 59–63 (1977).
Meyers, A.I., et al., "Separation of Diastereomers Using a Low Cost Preparative Medium–Pressure Liquid Chromatograph", J. Org. Chem., (1979), vol. 44, No. 13, p. 2247–2249.
Morrison et al Section 7.9—Reactions of chiral molecules with optically active reagents. Resolution, Organic Chemistry, 3rd Ed., Allyn and Bacon, Inc., Boston (1973).
Nakamura et al. Biochemistry, 24:1364–1376 (1985).
Narasaka et al. Tetrahedron, 40, 223–2238 (1984).
Pirkle, W.H. et al., "Broad Spectrum Methods for the Resolution of Optical Isomers. A Discussion of the Reasons Underlying the Chromatographic Separability of Some Diasteromeric Carbamates", J. Org. Chem,1977), vol. 42, No. 11, pp. 1839–1844.
Portoghese Relationships between Stereostructure and Pharmacological Activities, Elliott, H.W., Cutting, W.C., Dreisbach, R.H. (eds), Annual Review of Pharmacology, vol. 10, Annual Reviews Inc., Palo Alto, CA, pp. 51–76 (1970).
Prasad, K. et al., "Asymmetric synthesis of (3R–*trans*)– and (3S–cis)–hydroxy–5–pentanolides", Tetrahedron Letters, (1984), vol. 25, No. 32, pp. 3391–3394.
Prugh et al., Tetrahedron Letters 23: 281–284 (1982).
Ravin Chapter 75—Preformulation, Remington's Pharmaceutical Sciences, 16th Ed., Philadelphia College of Pharmacy and Science (1980).
Repta et al. Utilization of an Enantiomer as a Solution to a Pharmaceutical Problem: Application to Solubilization of I,2–Di(4–piperazine–2,6–dione)Propane, J. Pharm. Sci., vol. 65, pp. 238–242.
Robinson Absolute configurations of(–+–)–and (–)–1–amino 3–chloropropan–2–ol hydrochlorides, Chemistry and Industry, No. 15, p. 652 (1976).
Rosen, T. et al., "Tetrahedron Report Nu. 208—The Synthesis of Mevinic Acids", Tetrahedron, (1986), vol. 42, No. 18, pp. 4909–4951.

Roth et al. Tetrahedron Letters, vol. 29, No. 11, pp. 1255–1258 (1988).
Roth, Progress In Med. Chem., 40, 1–22 (2002).
Saigo, K. et al., "Optical Resolution of 2–Amino–1,2–diphenylethanol by Preferential Crystallization and Its Utilization in Fractional Crystallization and Enantioselective Reduction of Prochiral Ketones", Bull. Chem. Soc. Jpn., (1982) 55:1568–1573.
Schneider, C.S. et al., "Dopamine Autoreceptor Agonists: Resolution and Pharmacological Activity of 2,6–Diaminotetrahydrobenzothiazole and an Aminothiazole Analogue of Apomorphine", J. Med. Chem., (1987), 30:494–498.
Serizawa, N. et al., "Microbial Hydroxylation of ML–236B (Compactin) and Monacolin K (MG–530B)", J. Antibotics, (May 1983), 36:604–607.
Shaw, CDER FDA Guideline for Submitting Supporting Documentation in Drug Applications for the Manufacture of Drug Substances (1987).
Slater, E.E. et al., "Mechanism of Action and Biological Profile of HMG CoA Reductase Inhibitors, A New Therapeutic Alternative", Drugs, (1988) 36 (Suppl. 3):72–82.
Sletzinger, M. et al., "A Diasterospecific, Non–Racemic Synthesis of a Novel β–Hydroxy–δLactone HMG–CoA reductase Inhibitor", Tetrahedron Letters, (1985), vol. 26, No. 25, pp. 2951–2954.
Stokker et al., J. Med. Chem 28:347–358 (1985).
Stokker et al. J. Med. Chem. 1986, 29, 170–181.
Stokker et al. J. Org. Chem, 1986, 51, 4931–4934.
Stokker, G.E. et al., "3–Hydroxy–3–methylglutaryl– coenzyme A Reductase Inhibitors. 5. 6–(Fluoren–9–yl)– and 6–(fluoren–9–ylidenyl)–3,5–dihydroxyhexanoic acids and their lactone derivatives", J. Med. Chem., (May 1986), 29(5):852–855.
Streitwieser et al., Introduction to Organic Chemistry, Macmillan, New York, 3rd ed. 1985, p. 695.
Streitwieser Jr., A., "Stereoisomerism", Introduction to Organic Chemistry, Macmillan, New York, 3rd ed. 1985 Chapter 7, pp. 113–139.
Takano et al. Synthesis, Jul. 1989, vol. 7, p. 539–541.
The Merck Index, 10th Ed., (1983), entry 5949. N–Methylglucamine, p. 870–871.
The Merck Index, 12th Ed., (1996), entry 897. Atorvastatin, p. 146.
Tobert, J.A., "New developments in lipid–lowering therapy: the role of inhibitors of hydroxymethylglutarylcoenzyme A reductase", Circulation, (1987), 76, No. 3, 534–538.
Viret et al. Simple Optical Resolution of Terleucine, Tetrahedron Letters, vol. 27, No. 48, pp. 5865–5868 (1986).
Vollhardt Section 5–7—Resolution: The Separation of Enantiomers, in Organic Chemistry, W.H. Freeman and Company, New York (1987).
Vriesema, B.K. et al., "Resolution of 2–amino–5–thiomethyl pentanoic acid (homomethionine) with aminopeptidase from *pseudomonas putida*or chiral phosphoric acids", Tetrahedron Letters, (1986), vol. 26, No. 18, p. 2045–2048.
Walking, D. et al., "Decision Analysis in Drug Product Development", Drug & Cosmetic Industry, (1973) 112(3):39–41.
Weissbuch, I. et al., "Design of Polymeric Inhibitors for the Control of Crystal Polymorphism. Induced Enantiomeric Resolution of Racemic Histidine by Crystallization at 25° C.", J. Am. Chem. Soc., (1987) 109:1869–1871.
Wells Pharmaceutical Preformulation: The Physicochemical Properties of Drug Substances—Chapter 2 (1988).
Whilen Topics in Stereochemistry, 6, 107–1776 (1971).
Wilen et al. Tetrahedron, 33, 2725–2736 (1977).
Willaims, K.M., "Chirality: Pharmacokinetics and Pharmacodynamics in 3 Dimensions", Clinical and Experimental Pharmacology and Physiology, (Jun. 1989), vol. 16, No. 6, pp. 465–470.
Witiak et al. Pharmaceuticals, Optically Active, Encyclopedia of Chemical Technology, 3ed, vol. 17, 311–345 (1982).
Wong, C–H. et al., "Mutual Resolution of (±)–ephedrine and Z–DL–Amino Acid Induced by Seeding Chiral Salt", Tetrahedron Letters No. 40, (1978), p. 3813–3816.
Yang, Y–L, et al., "Mevinic Acids and Analogues: Preparation of a Key Chiral Intermediate", Tetrahedron Letters, (1982), vol. 23, No. 42, pp. 4305–4308.
Yoshino et al. Diabetes Research and Clinical Practice 2 (1986) 179–181.
*Pfizer Inc, et al.* v. *Ranbaxy Pharmaceuticals Limited, et al.*, 457 F 3d 1284 (Fed. Cir. 2006) (Exhibit 1 to Preliminary Amendment).
*Pfizer Inc, et al.* v. *Ranbaxy Pharmaceuticals Limited, et al.*, 405 F. Supp. 2d 495 (D. Del. 2005) (Exhibit 2 Preliminary Amendment).
"Pfizer's Proposed Findings of Fact", CA No. 03–209–JJF (Exhibit 3 to Preliminary Amendment).
"Pfizer's Proposed Supplemental Findings of Fact", CA No. 03–209–JJF (Exhibit 4 to Preliminary Amendment).
"Pfizer's Proposed Conclusions of Law", CA No. 03–209–JJF (Exhibit 5 to Preliminary Amendment).
"Pfizer's Proposed Supplemental Conclusions of Law", CA No. 03–209–JJF (Exhibit 6 to Preliminary Amendment).
"Opening Proposed Findings of Fact and Conclusions of Law of Defendants Ranbaxy Laboratories Limited and Ranbaxy Pharmaceuticals Inc.", CA No. 03–209–JJF (Exhibit 7 to Preliminary Amendment).
"Petition for Panel Rehearing and Petition for Rehearing En Banc by Defendants–Appellants Ranbaxy Laboratories Limited and Ranbaxy Pharmaceuticals Inc." No. 2006–1179 (Exhibit 8 to Preliminary Amendment).
"Plaintiff–Appellee's Response to Petition for Rehearing En Banc", No. 2006–1179 (Exhibit 9 to Preliminary Amendment).
"Order" denying Request for Panel Rehearing and Rehearing En Banc (Exhibit 10 to Preliminary Amendment).
"Pfizer's Post–Trial Opening Brief", CA No. 03–209–JJF (Exhibit 11 to Preliminary Amendment).
"Opening Post–Trial Brief of Defendants Ranbaxy Laboratories Limited and Ranbaxy Pharmaceuticals Inc.", CA No. 03–209–JJF (Exhibit 12 to Preliminary Amendment).
"Pfizer's Corrected Post–Trial Reply Brief", CA No. 03–209–JJF (Exhibit 13 to Preliminary Amendment).
"Defendant Ranbaxy Laboratories Limited and Ranbaxy Pharmaceuticals Inc.'s Opposition Post–Trial Brief", CA No. 03–209–JJF (Exhibit 14 to Preliminary Amendment).
Summaries of Non–United States Proceedings Involving Counterparts to U.S. Patent No. 5,273,995, including: i) List of Countries (3 sheets); ii) Table of Foreign Lawsuits (5 sheets); and iii) Lipitor Canada Enantiomer Cases Document Schedules (28 sheets) (Exhibit 15 to Preliminary Amendment).
"Brief of Defendants–Appellants Ranbaxy Laboratories Limited and Ranbaxy Pharmaceuticals, Inc." No. 06–1179 (Exhibit 16 to Preliminary Amendment).

"Brief of Plaintiffs–Appellees, Pfizer Inc." No. 06–1179 (Exhibit 17 to Preliminary Amendment).
"Reply Brief of Defendants–Appellants Ranbaxy Laboratories Limited and Ranbaxy Pharmaceuticals, Inc." No. 06–1179 (Exhibit 18 to Preliminary Amendment).
*Sanofi–Synthelabo et al.* v. *Apotex, Inc. et al.*, No. 06–1613 (Fed. Cir. Dec. 8, 2006) (Exhibit 20 to Preliminary Amendment).
US 5,273,995 prosecution history, marked as Defendant's Trial Exhibit 139 in CA No. 023–209 (D. Del.) and comprising pages stamped RA0147320–RA014884 (Exhibit 22 to Preliminary Amendment).
CA 1,330,441 file history which includes Canadian Patent Application No. 590,367 as filed Feb. 7, 1989.
CA 2,021,546 file history.
European Patent Application 87 107 847.3 file history.
European Patent Application 90 113 986.5 Claims (part of EP 0409281 file history C152).
European Patent Application 90 113 986.5 Claims as granted (part of EP 0409281 file history C152).
European Patent Application 90 113 986.5 (Jan. 25, 2000 Communication) (part of EP 0409281 file history C152).
European Patent Application 90 113 986.5 Refusal (Sep. 5, 1998) (part of EP 0409281 file history C152).
European Patent Application 90 113 986.5 file history.
EP 0409281 file history.
US 4,618,893 file history.
US 5,003,080 file history.
CTT Collaborators, "Efficacy and Safety of Cholesterol–Lowering Treatment: Prospective Meta–Analysis of Data from 90 056 Participants in 14 Randomised Trials of Statins", The Lancet, 2005, Vol. 366, pp. 1267–1278.
*Pfizer Inc.*v. *Ranbaxy Labs. Ltd.*, 405 F. Supp. 2d 495 (D. Del. 2005).
*Pfizer Inc.* v. *Ranbaxy Labs. Ltd.* , 457 F.3d 1284 (Fed. Cir. 2006).
Berge, Stephen M. et al., "Pharmaceutical Salts," *Journal of Pharm. Science*, vol. 66, No. 1 (Jan. 1, 1977).
"Guidelines For Submitting Supporting Documentation in Drug Applications For The Manufacture of Drug Substances," Center for Drug Evaluation and Research, Food and Drug Administration, Department of Health and Human Services, Feb. 1987.
*Ranbaxy Australia Pty. Ltd.* v. *Warner–Lambert Co. LLC*, decision by The Federal Court of Australia (Dec. 20, 2006).
*Pfizer Canada Inc.* v. *The Minister of Health and Ranbaxy Labs. Ltd.*, 2007 FC 91 (Jan. 25, 2007).
Letter of Aug. 19, 1998 from US PTO to Francis J. Tinney regarding patent extension for Lipitor.
Letter of Nov. 7, 2005 from William Curatolo of Pfizer Global Research & Development and Stephen R. Bym of SSCI, Inc. to the Division of Dockets Management, food and Drug Administration, entitled Citizen Petition.
NOC listings for rosuvastatin, fluvastatin, pravastatin, lovastatin, atorvastatin, simvastatin, cerivastatin.
Ranbaxy Reply in Support of Petition for Certiorari (Exhibit 25 to Supplemental Communication).
Supreme Court decision denying Certiorari (Exhibit 26 to Supplemental Communication).
Ranbaxy's Apr. 12, 2007 ANDA Notice Letter (Exhibit 27 to Supplemental Communication).
Pfizer Complaint (138 Delaware Action) (Exhibit 28 to Supplemental Communication).
Ranbaxy Amended Answer and Counterclaims (138 Delaware Action) (Exhibit 29 to Supplemental Communication).
Pfizer Reply to Ranbaxy's Amended Answer (138 Delaware Action) (Exhibit 30 to Supplemental Communication).
Pfizer Briefs in Support of Motions to Dismiss (138 Delaware Action) (Exhibit 31 to Supplemental Communication).
Ranbaxy Responses to Motions to Dismiss (138 Delaware Action) (Exhibit 32 to Supplemental Communication).
Teva ANDA Notice Letter (Exhibit 33 to Supplemental Communication).
KSR decision (Exhibit 34 to Supplemental Communication).
Commissioner's Memorandum re: KSR decision (Exhibit 35 to Supplemental Communication).
*Pfizer* v. *Apotex* decision (Exhibit 36 to Supplemental Communication).
Order Denying Rehearing, and Dissents,in *Pfizer* v. *Apotex* decision (Exhibit 37 to Supplenental Communication).
Danish decision, Engllish translation (Exhibit 38 to Supplemental Communication).
Australian decision, *Ranbaxy Australia* v. *Warner–Lambert Co. LLC* (Exhibit 39 to Supplemental Communication).
Canada decision, Docket T–507–05, dated Jan. 25, 2007 (Exhibit 40 to Supplemental Communication).
*Pfizer Canada* v. *Canada* (*Minister of Health*), 2006 F.C. 1471 (Exhibit 41 to Supplemental Communication).
EPO Technical Opinion (Exhibit 42 to Supplemental Communication).
Pfizer Complaint (Exhibit 43 to Supplemental Communication).
Wanner, C., et al., "Atorvastatin in Patients with Type 2 Diabetes Mellitus Undergoing Hemodialysis", The New England Journal of Medicine, 2005, vol. 353, No. 3, pp. 238–248.
Patti, G., et al., "Randomized Trial of Atorvastatin for Reduction of Postoperative Atrail Fibrillation in Patients Undergoing Cardiac Surgery. Results of the ARMYDA–3 (Atorvastatin for Reduction of Myocardial Dysrhythmia After Cardiac Surgery", Circulation, 2006, vol. 114, pp. 1455–1461.
"Management of Dyslipidemia in Adults with Diabetes", Diabetes Care, 2003, vol. 26, Supp. 1, pp. S83–S86.
"Summary of Revisions for the Clinical Practice Recommendations", Diabetes Care, 2005, vol. 28, Supp. 1, p. S3.
"Standards of Medical Care in Diabetes–2008", Diabetes Care, 2008, vol. 31, Supp. 1, pp. S12–S54.
Smith, S. C., et al., "AHA. ACC Guidelines for Secondary Prevention for Patients with Coronary and Other Atherosclerotic Vascular Disease: 2006 Update", J. Am. Coll. Cardiol., 2006, vol. 47, No. 10, pp. 2130–2139.
Koren, M. J., et al., "Clinical Outcomes in Managed–Care Patients with Coronary Heart Disease Treated Aggressively in Lipid–Lowering Disease Management Clinics", Journal of the American College of Cardiology, 2004, vol. 44, No. 9, pp. 1772–1779.
Patti, G., et al., "Atorvastatin Pretreatment Improves Outcomes in Patients with Acute Coronary Syndromes Undergoing Early Percutaneous Coronary Intervention", Journal of the American College of Cardiology, 2007, vol. 49, No. 12, pp. 1272–1278.
van Wissen, S., et al., "Long–Term Safety and Efficacy of High–Dose *Atorvastatin Treatment* in Patients with Familial Hypercholesterolemia", The American Journal of Cardiology, 2005, vol. 95, pp. 264–266.

Sever, P. S., et al., "The Anglo–Scandinavian Cardiac Outcomes Trial Lipid Lowering Arm: Extended Observations 2 Years After Trial Closure", European Heart Journal, 2007, pp. 1–10.

Raal, F. J., et al., "A Single–Centre Retrospective Observational Study to Evaluate the Change in Total Cholesterol and LDL Cholesterol in Hyperlipidaemic Patients Switched from Atorvastattin to Simvastatin", Cardiovascular Journal of South Africa, 2004, vol. 15, No. 3, pp. 118–123.

Knopp, R. H., et al., "Efficacy and Safety of Atorvastatin in the Prevention of Cardiovascular End Points in Subjects with Type 2 Diabetes", Diabetes Care, 2006, vol. 29, No. 7, pp. 1478–1485.

McKenney, J. M., et al., "Use of a Treatment Algorithm to Achieve NCEP ATP III Goals with Atorvastatin", J. Cardiovasc Pharmacol. 2005, vol. 46, No. 5, pp. 594–599.

Gresser, U., et al., "Atorvastatin: Gold Standard for Prophylaxis of Myocardial Ischemia and Stroke", European Journal of Medical Research, 2004, vol. 9, pp. 1–17.

Bone, H. G., "Effects of Atorvastatin on Bone in Postmenopausal Women with Dyslipidemia: A Double–Blind, Placebo–Controlled, Dose–Ranging Trial", The Journal of Clinical Endocrinology & Metabolism, 2007, vol. 92, No. 12, pp. 4671–4677.

Colhoun, H. M., et al., "Primary Prevention of Cardiovascular Disease with Atorvastatin in Type 2 Diabetes in the Collaborative Atorvastatin Diabetes Study (CARDS): Multicentre Randomised Placebo–Controlled Trial", The Lancet, 2004, vol. 364, pp. 685–696.

CTT Collaborators, "Efficacy of Cholesterol–Lowering Therapy in 18,686 People with Diabetes in 14 Randomised Trials of Statins: A Meta–Analysis", The Lancet, 2008, vol. 371, pp. 117–125.

Pedersen, T. R., et al., "High–Dose Atorvastatin vs Usual–Dose Simvastatin for Secondary Prevention After Myocardial Infarction", JAMA–Express, 2005, vol. 294, No. 19, pp. 2437–2445.

Law, M. R., et al., "Quantifying Effect of Statins on Low Density Lipoprotein Cholesterol, Ischaemic Heart Disease, and Stroke: Systematic Review and Meta–Analysis", BMJ, 2003, vol. 326, pp. 1–7.

McCrindle, B. W., et al., "Efficacy and Safety of Atorvastatin in Children and Adolescents with Familial Hypercholesterolemia or Severe Hyperlipidemia: A Multicenter, Randomized, Placebo–Controlled Trial", The Journal of Pediatrics, 2003, vol. 142, pp. 74–80.

Jones, P. H., et al., "Comparison of the Efficacy and Safety of Atorvastatin Iniitated at Different Starting Doses in Patients with Dyslipidemia", American Heart Journal, 2005, vol. 149, pp. 111e1–111e8.

Ncep, "Detection, Evaluation, and Treatment of High Blood Cholesterol in Adults (Adult Treatment Panel III) Final Report", National Institutes of Health, 2002, pp. I–1 through Ref.–49.

Larosa, J. C., et al., "Intensive Lipid Lowering Atorvastatin in Patients with Stable Coronary Disease", The New England Journal of Medicine, 2005, vol. 352, pp. 1–11.

"KDOQI Clinical Practice Guidelines and Clinical Practice Recommendations for Diabetes and Chronic Kidney Disease", American Journal of Kidney Diseases, 2007, vol. 49, No. 2, Suppl. 2, pp. S1–S179.

Cannon, C. P., et al., "Comparison of Intensive and Moderate Lipid Lowering with Statins After Acute Coronary Syndromes", The New England Journal of Medicine, 2004, vol. 350, No. 15, pp. 1–10.

Deedwania, P., et al., "Effects of Intensive Versus Moderate Lipid–Lowering Therapy on Myocardial Ischemia in Older Patients with Coronary Heart Disease: Results of the Study Assessing Goals in the Elderly (SAGE)", Circulation, 2007, vol. 155, pp. 700–707.

Adams, R. J., et al., "Update to the AHA/ASA Recommendation for the Prevention of Stroke in Patients with Stroke and Transient Ischemic Attack", Stroke, 2008, vol. 39, pp. 1–6.

Sparcl Investigators, "High–Dose Atorvastatin After Stroke or Transient Ischemic Attack", The New England Journal of Medicine, 2006, vol. 355, No. 6, pp. 1–11.

McCarey, D. W., et al., "Trial of Atorvastatin in Rheumatoid Arthritis (TARA): Double–Blind, Randomised–Placebo–Controlled Trial", The Lancet, 2004, vol. 363, pp. 2015–2021.

LaRosa, J. C., et al., "Safety and Efficacy of *Atorvastatin* – Induced very Low–Density Lipoprotein Cholesterol Levels in Patients with Coronary Heart Disease (A Post Hoc Analysis of the Treating to New Targets [TNT]Study", Am J Cardiol, 2007, vol. 100, pp. 747–752.

Shepherd, J., et al., "Effect of Intensive Lipid Lowering with Atorvastatin on Renal Function in Patients with Coronary Heart Disease: The Treating to New Targets (TNT) Study", Clin J Am Soc Nephrol. ePress, 2007, vol. 2, pp. 1131–1139.

Waters, D. D., et al., "Effects of High–Dose Atorvastatin on Cerebrovascular Events in Patients with Stable Coronary Disease in the TNT (Treating to New Targets) Study", Journal of the American College of Cardiology, 2006, vol. 48, No. 9, pp. 1973–1799.

Khush, K. K., et al., "Effect of High–Dose Atorvastatin on Hospitalizations for Heart Failure", Circulation, 2007, vol. 115, pp. 576–583.

Phillips, B., et al., "Switching Statins: The Impact on Patient Outcomes", The British Journal of Cardiology, 2007, vol. 14, pp. 280–285.

Ford, I., et al., "Long–Term Follow–Up of the West of Scotland Coronary Prevention Study", The New England Journal of Medicine, 2007, vol. 357, No. 15, pp. 1477–1486.

Decision of the Federal Court of Australia, dated May 28, 2008.

Notice of Intent to Issue Ex Parte Reexamination Certificate, dated Apr. 29, 2008, in Reexamination of US. Pat No. 4,681, 893.

Consent Judgement and Order of the Court, dated May 15, 2008, in *Pfizer Inc. et al.* v. *Cobalt Pharmaceuticals*.

Foody et al, Clinical Therapeutics 30: 195 (2008).

Transcript of Testimony of Dr. James Bowman from Delaware Lipitor trial, given Dec. 12, 2004.

Tobert, J.A. et al, "Cholesterol–lowering Effect of Mevinolin, an Inhibitor of 3–hydroxyl–3–methylglutaryl–Coenzyme A Reductase, in Healthy Volunteers", J. Clin. Invest. 69:913 (1982).

"Petition for a Writ of Certiorari," *Ranbaxy Laboratories Limited et al.* v. *Pfizer Inc. et al.*, No. 06–1179, Jan. 22, 2007. (Exhibit 23 to Supplemental Communication).

Pfizer Opposition to Ranbaxy Petition for Certiorari, Feb. 26, 2007. (Exhibit 24 to Supplemental Communication).

Complaint, Civil Action No. 07–790, United States District Court for the District of Deleware, Dec. 6, 2007 (without exhibits).

Complaint, Civil Action No. 1:07–cv–12257, United States District Court for the District of Massachusetts, Dec. 7, 2007 (without exhibits).

English Language version of DK 171588 B1 (Feb. 10, 1997).

Exhibit 60—Opinion of Delaware District Court—Ranbaxy Caduet® Case (Nov. 29, 2007).

J. W. Hubbard et al.; Clinical Biochemistry, vol. 19, pp. 107–112 (Apr. 1986).

Exhibit 15C—Updates and Corrections to Previous Exhibits 15, 15A and 15B.

German Decision, Oct. 29, 2007 (English translation).

Cobalt Pharmaceuticals, Paragraph IV Certification, Oct. 24, 2007.

Mar. 20, 2008 Decision of Federal Court of Appeal(Canada) in Proceedings Between (Pfizer Canada Inc. and Warner–Lambert Company, LLC) and (The Minister of Health and Ranbaxy Laboratories Limited); Case Caption: A–79–07 (Citation: 2008 FCA 108).

English Language translation of ruling by The Court of Appeal of the Hague (Feb. 28, 2008).

Joint Stipulation; Civil Action No. 07–360 (JJF) (filed Jan. 28, 2008, so ordered Jan. 30, 2008).

Joint Stipulation; Civil Action No. 07–360 (JJF) (filed Mar. 10, 2008, so ordered Mar. 11, 2008).

Response to Non–Final Office Action in Reexamination of '893 Patent (Control No. 90/008,727) dated Mar. 7, 2008.

Third Information Disclosure Statement in Reexamination of '893 Patent (Control No. 90/008,727) dated Mar. 7, 2008.

Answer, Affirmative Defenses and Counterclaims of Defendant Cobalt Pharmaceuticals, Inc.; C.A. No. 07–790–JJF (Jan. 25, 2008).

Reply to Counterclaims; C.A. No. 07–790–JJF (Feb. 22, 2008).

Certified English language translation of Apr. 7, 2008 Decision of Provincial Court of Barcelona (Spain); Appeal from Commercial Court decision; Parties—Krn Pharma, S.L.; Laboratorios Cinfa, S.A. et al. and Warner–Lambert Company et al.; Judgement 184/2007–2.

Second ANDA Notice Letter from Teva Pharmaceuticals USA, Inc. to Pfizer, Inc and Warner–Lambert Company (Mar. 12, 2008).

Stipulated Amended Order of Final Judgement in Civil Action No. 07–138 (JJF) (Dec. 13, 2007).

First Office Action in Reexamination of '893 Patent (Control No. 90/008,727) dated Jan. 10, 2008.

Jan. 4, 2008 Decision of Canadian Court in Proceedings Between (Pfizer Canada Inc. and Warner–Lambert Company, LLC) and (The Minister of Health and Apotex Inc.); Case Caption: T–16–06.

"Examination Guidelines for Determining Obviousness Under 35 U.S.C. § 103 in View of Supreme Court Decision in *KSR International Co.* v. *Teleflex Inc.* , " 72 Fed. Reg. 57526 (Oct. 10, 2007).

*Aventis Pharma Deutschland GmbH* v. *Lupin Pharmaceutical , Inc.* , 799 F. 3d 1293 (Fed. Cir. Sep. 11, 2007).

*Aventis Pharma Deutschland Gmbh.* v. *Lupin Pharmaceuticals, Inc.* , 2006 U.S. Dist. Lexis 48246 (E.D.Va. 2006).

Alberts et al., PNAS USA 77:3957 (1980).

Illingworth and Bacon, Am. J. Cardiol. 30:33G (1987).

"Consent Order and Stipulated Injunction" in C.A. No. 07–cv–138–JJF ("Caduet® case") dated Jun. 20, 2008.

* cited by examiner

[R-(R*R*)]-2-(4-FLUOROPHENYL)-β,δ-DIHYDROXY-5-(1-METHYLETHYL-3-PHENYL-4-[(PHENYLAMINO)CARBONYL]-1H-PYRROLE-1-HEPTANOIC ACID, ITS LACTONE FORM AND SALTS THEREOF

Matter enclosed in heavy brackets [ ] appears in the original patent but forms no part of this reissue specification; matter printed in italics indicates the additions made by reissue.

*Notice: More than one reissue application has been filed for the reissue of Pat. No. 5,273,995. U.S. application Ser. No. 11/973,897, filed on Oct. 10, 2007, is a continuation reissue of U.S. application Ser. No. 11/653,830 (the instant application), filed on Jan. 16, 2007, which is a reissue of U.S. application Ser. No. 07/660,976, filed Feb. 26, 1991, now U.S. Pat. No. 5,273,995.*

This is a continuation of U.S. application Ser. No. 07/384,187 filed Jul. 21, 1989, abandoned.

BACKGROUND OF THE INVENTION

Trans-(±)-5-(4-fluorophenyl)-2-(1-methylethyl)-N,4-diphenyl-1-[2-tetrahydro-4-hydroxy-6-oxo-2H-pyran-2-yl)ethyl]-1H-pyrrole-3-carboxamides are among compounds of U.S. Pat. No. 4,681,893 having usefulness as inhibitors of cholesterol biosynthesis. The compounds therein broadly include 4- hydroxypyran-2-ones and the corresponding ring-opened acids derived therefrom.

It is now unexpectedly found that the enantiomer having the R form of the ring-opened acid of trans-5-(4-fluorophenyl)-2-(1-methylethyl)-N,4-diphenyl-1-[2-tetrahydro-4-hydroxy-6-oxo-2H-pyran-2-yl)ethyl]-1H-pyrrole-3-carboxamide; that is [R-(R*,R*)]-2-(4-fluorophenyl)-β,δ-dihydroxy-5-(1-methylethyl)-3-phenyl-4-[(phenylamino)carbonyl]-1H-pyrrole-1-heptanoic acid, provides surprising inhibition of the biosynthesis of cholesterol.

It is known that 3-hydroxy-3-methylglutaryl coenzyme A (HMG-CoA) exists as the 3R-stereoisomer. Additionally, as shown in the study of a series of 5-substituted 3,5-dihydroxypentanoic acids by Stokker et al., in "3-Hydroxy-3-methylglutaryl-Coenzyme A Reductase Inhibitors. 1. Structural Modification of 5-Substituted 3,5-Dihydroxypentanoic acids and Their Lactone Derivatives," J. Med. Chem. 1985, 28, 347-358, essentially all of the biological activity resided in the trans diastereomer of (E)-6-[2-(2,4-dichlorophenyl)ethenyl]-3,4,5,6-tetrahydro-4-hydroxy-2H-pyranone having a positive rotation. Further, the absolute configuration for the β-hydroxy-δ-lactone moiety common to mevlnolin of the formula (1a)

1a

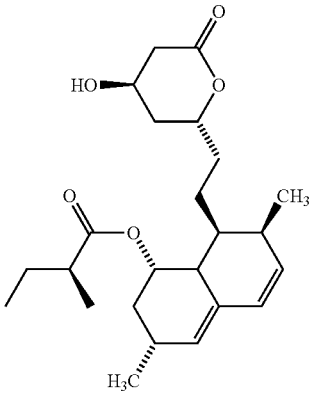

and compactin of the formula (1b)

-continued

1b

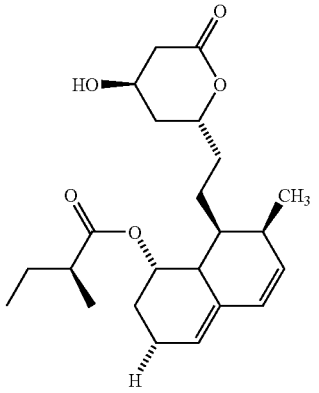

apparently is required for inhibition of HMG-CoA reductase. This is reported by Lynch et al. in "Synthesis of an HMB-CoA Reductase Inhibitor; A diastereoselective Aldol Approach in Tetrahedron Letters, Vol. 28, No. 13, pp. 1385-1388 (1987) as the 4R, 6R configuration.

However, an ordinarily skilled artisan may not predict the unexpected and surprising inhibition of cholesterol biosynthesis of the present invention in view of these disclosures.

SUMMARY OF THE INVENTION

Accordingly the present invention provides for compounds consisting of [R-(R*,R*)]-2-(4-fluorophenyl)-β,δ-dihydroxy-5-((1-methylethyl)-3-phenyl-4-[(phenylamino) carbonyl]-1H-pyrrole-1-heptanoic acid (compound of formula I), pharmaceutically acceptable salts thereof and (2R-trans)-5-(4-fluorophenyl)-2-(1-methylethyl)-N,4-diphenyl-1-[2-(tetrahydro-4-hydroxy-6-oxo-2H-pyran-2-yl) ethyl]-1H-pyrrole-3-carboxamide (the lactone form of the heptanoic acid or compound of formula II).

The present invention also relates to a pharmaceutical composition, useful as a hypocholesterolemic agent, comprising a hypocholesterolemic effective amount of [R-(R*,R*)]-2-(4-fluorophenyl)-β,δ-dihydroxy-5-(1-methylethyl)-3-phenyl-4-[(phenylamino)carbonyl]-1H-pyrrole-1-heptanoic acid, its pharmaceutically acceptable salts of (2R-trans)-5-(4-fluorophenyl)-2-(1-methylethyl-N,4-diphenyl-1-[2-(tetrahydro-4-hydroxy-6-oxo-2H-pyran-2-yl)ethyl]-1H-pyrrole-3-carboxamide acid; and a pharmaceutically acceptable carrier. Further, the present invention is also a method of treating mammals, including humans, suffering from hypercholesterolemia by administering to such mammal a dosage form of the pharmaceutical composition described above.

DETAILED DESCRIPTION OF THE INVENTION

The pharmaceutically acceptable salts of the invention are those generally derived by dissolving the free acid or the lactose; preferably the lactone, in aqueous or aqueous alcohol solvent or other suitable solvents with an appropriate base and isolating the salt by evaporating the solution or by reacting the free acid or lactone; preferably the lactone and base in an organic solvent in which the salt separates directly or can be obtained by concentration of the solution.

In practice, use of the salt form amounts to use of the acid or lactone form. Appropriate pharmaceutically acceptable salts within the scope of the invention are those derived from bases such as sodium hydroxide, potassium hydroxide, lithium hydroxide, calcium hydroxide, 1-deoxy-2-(methylamino)-D-glucitol, magnesium hydroxide, zinc hydroxide, aluminum hydroxide, ferrous or ferric hydroxide, ammonium hydroxide or organic amines such as N-methylglucamine, choline, arginine and the like. Preferably, the lithium, calcium, magnesium, aluminum and ferrous or ferric salts are prepared from the sodium or potassium salt by adding the appropriate reagent to a solution of the sodium or potassium salt, i.e., addition of calcium chloride to a solution of the sodium or potassium salt of the compound of the formula I will give the calcium salt thereof.

The free acid can be prepared by hydrolysis of the lactone form of formula II or by passing the salt through the cationic exchange resin (H+resin) and evaporating the water.

The most preferred embodiment of the present invention is [R-(R*R*)]-2-(4-fluorophenyl)-β,δ-dihydroxy-5-(1-methylethyl)-3-phenyl-4-[(phenylamino)carbonyl]-1H-pyrrole-1-heptanoic acid, hemicalcium salt.

Generally, the compounds I and II of the present invention may be prepared by the processes described in U.S. Pat. No. 4,681,893 which is incorporated by reference therefor, or (2) synthesizing the desired chiral form beginning from starting materials which are known or readily prepared using processes analogous to those which are known.

Specifically, resolution of the racemate may be accomplished as shown in Scheme I (where Ph is phenyl) as follows:

Scheme 1

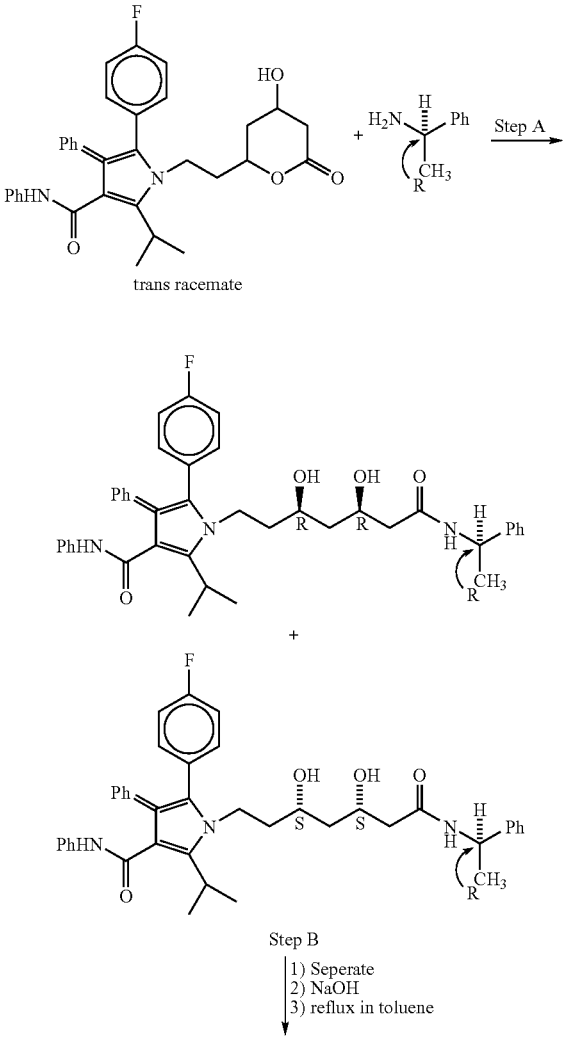

-continued

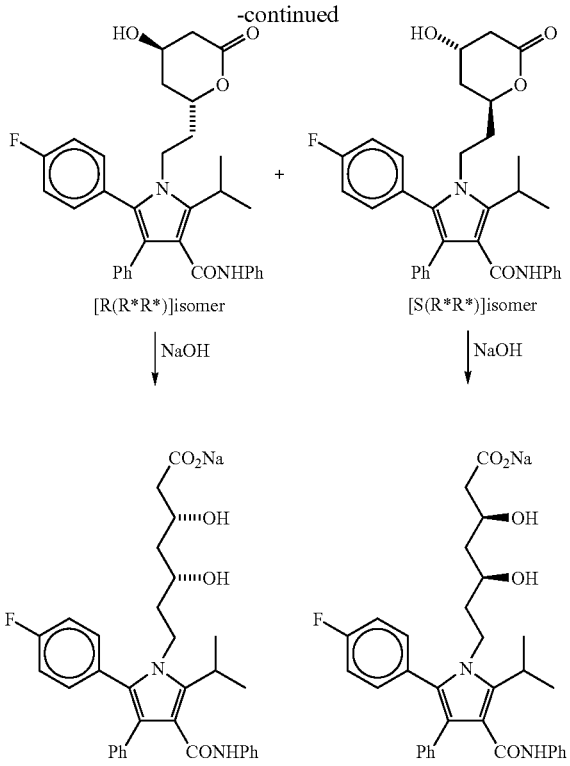

The "trans racemate" of Scheme 1 means a mixture of the following:

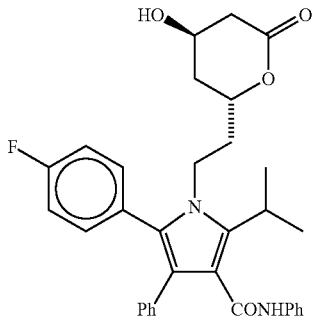

[R(R*R*)]isomer and

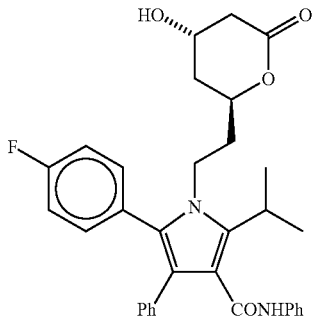

[S(R*R*)]isomer

Scheme 2
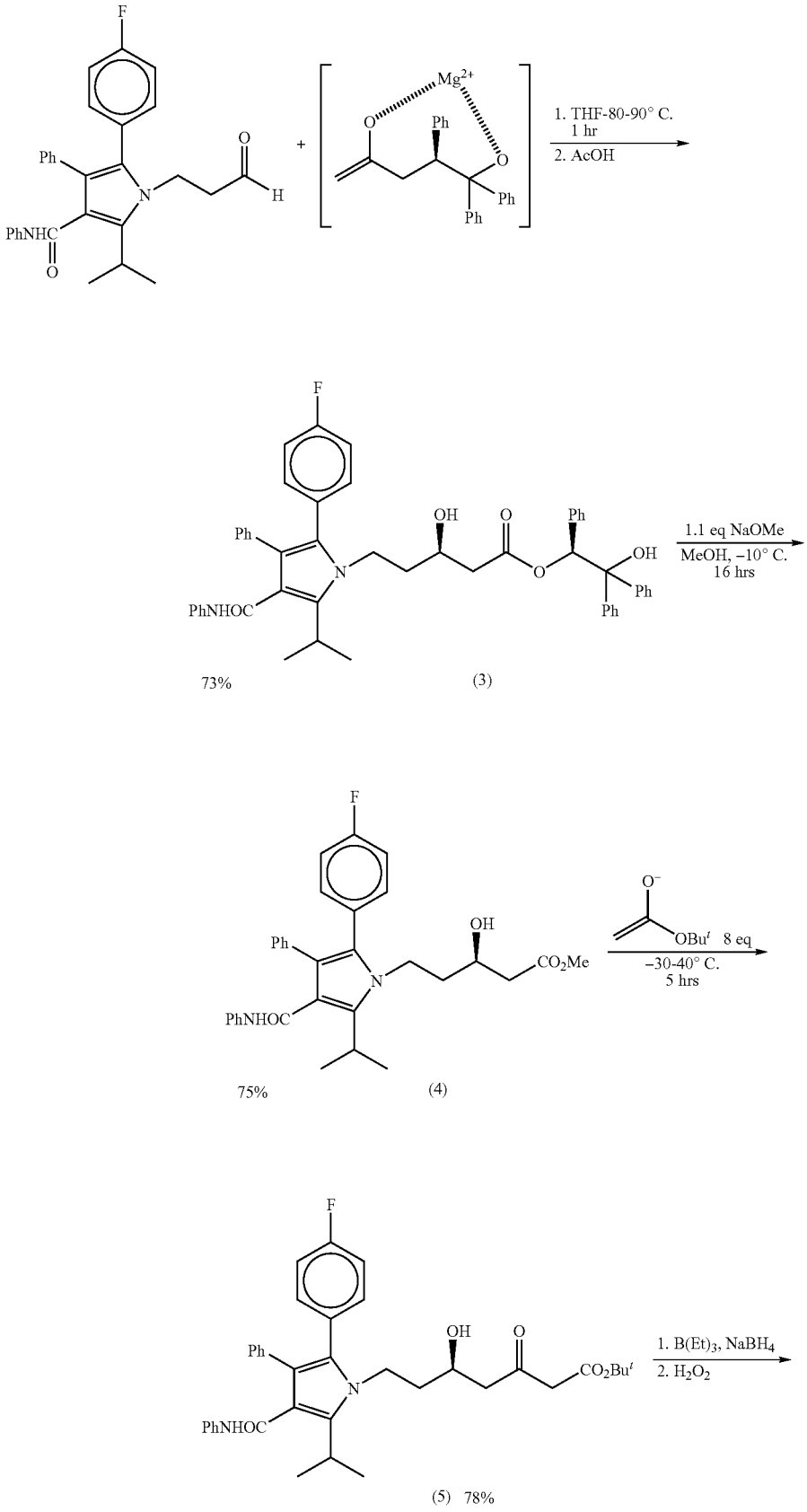

-continued

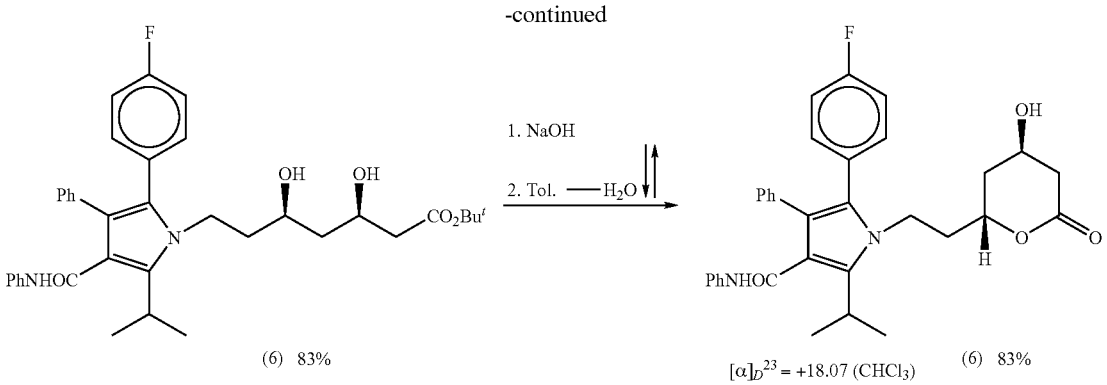

Generally, conditions for Scheme 2 are as shown in the Examples 1–5 hereinafter.

One of ordinary skill in the art would recognize variations in the Schemes 1 and 2 which are appropriate for the preparation of the compounds of the present invention.

The compounds according to present invention and especially according to the compound of the formula I inhibit the biosynthesis of cholesterol as found in the CSI screen that is disclosed in U.S. Pat. No. 4,681,893 which is now also incorporated by reference therefor. The CSI data of the compound I, its enantiomer the compound II and the racemate of these two compounds are as follows:

| Compound | $IC_{50}$ (micromoles/liter) |
|---|---|
| [R—(R*R*)] isomer | 0.0044 |
| [S—(R*R*)] isomer | 0.44 |
| Racemate | 0.045 |

Accordingly, the present invention is the pharmaceutical composition prepared from the compound of the formula I or II or pharmaceutically acceptable salts thereof.

These compositions are prepared as described in U.S. Pat. No. 4,681,893 which is, therefore, again incorporated by reference here.

Likewise, the present invention is a method of use as hypolipidemic or hypocholesterolemic agents. The compounds of the present invention utilized in the pharmaceutical method of this invention are administered to the patient at dosage levels of from 10 to 500 mg per day which for a normal human adult of approximately 70 kg is a dosage of from 0.14 to 7.1 mg/kg of body weight per day. The dosages may be preferably from 0.5 to 1.0 mg/kg per day.

The dosage is preferably administered as a unit dosage form. The unit dosage form for oral or parenteral use may be varied or adjusted from 10 to 500 mg, preferably from 20 to 100 mg according to the particular application and the potency of the active ingredient. The compositions can, if desired, also contain other active therapeutic agents. Determinations of optimum dosages for a particular situation is within the skill of the art.

The compounds of the formula I and II and their pharmaceutically acceptable salts are in general equivalent for the activity of the utility as described herein.

The following examples illustrate particular methods for preparing compounds in accordance with this invention. These examples are thus not to be read as limiting the scope of the invention.

EXAMPLE 1

285 ml 2.2M n-butyl lithium (in Hexane) is added dropwise to 92 ml diisopropylamine in 300 ml THF at 50°–60° C. in a 1000 ml 1 neck flask via dropping funnel and under nitrogen. The well stirred yellow solution is allowed to warm to about −20° C. Then it is cannulated into a suspension of 99 g S(+)-2-acetoxy-1,1,2-triphenylethanol in 500 ml absolute THF, kept in a 2L-3 neck flask at −70° C. When addition is complete, the reaction mixture is allowed to warm to −10° C. over a period of two hours. Meanwhile, a suspension of 0.63 mol $MgBr_2$ is prepared by dropping 564 ml (0.63 mol) of bromine into a suspension of 15.3 g of magnesium (0.63 mol) in 500 ml THF plus in 3 L flask equipped with reflux condenser, and overhead stirrer. When this is completed, the $MgBr_2$ suspension is cooled to −78° C. and the enolate solution (dark brown) is cannulated into the suspension within 30 minutes. Stirring is continued for 60 minutes at −78° C. 150 g 5-(4-fluorophenyl)-2-(1-methylethyl)-1-(3-oxopropyl)-N,4-diphenyl-1H-pyrrole-3-carboxamide in 800 ml THF absolute was added dropwise over 30 minutes; then stirred for 90 minutes at −78° C., then quenched with 200 ml AcOH at −78° C. This is removed to a cool bath, 500 ml of $H_2O$ is added and the mixture concentrated in vacuo at 40°–50° C. 500 ml of 1:1 EtOAc/Heptane is added to the yellowish slurry and filtered. The filtrate is washed extensively with 0.5N HCl, then several times with $H_2O$ and finally with EtOAc/Heptane (3:1) that was cooled with dry ice to −20° C. The light brown crystalline product (Example 1A) is dried in vacuum oven at 40° C. The yield is 194 g.

The product 1A is recrystallized from EtOAc at −10° C. to yield 100 g to yield product 1B and then recrystallized from acetone/pentane to yield 90 g to yield product 1C. The mother liquor is combined from the wash of the crude material and recrystallized from EtOAc/Hexane. 33 g of 1B shows the following: HPLC: 97.4:2.17 of the R,S to S,S isomers. 28.5 g of 1C shows the following: HPLC:95.7:3.7. The combined 1B and 1C is recrystallized from $CHCl_3$ MeOH 10:1; providing a product 1F having a yield of 48.7 g of white crystal.

The mother liquor of the first aqueous wash is crystallized (EtOAc/Heptane) to yield product 1D of 21.4 g; HPLC: 71.56:25.52.

The mother liquor of 1B and 1C is combined and recrystallized from $CHCl_3$/MeOH/Heptane to yield 55.7 g white crystals of product 1G.

1D is recrystallized from $CHCl_3$/MeOH to yield the product 1H.

All mother liquor is combined, concentrated then the residue is dissolved in hot $CHCl_3$/MeOH 10:1; put on a silica gel column; and eluted with EtOAc/Hexane 40:60. The material crystallized out on the column and the silica gel is extracted with $CHCl_3$/MeOH and concentrated. Recrystallization of the residue from $CHCl_3$/Heptane 3:1 yields 33.7 g of product 1I.

The mother liquor of 1I is recrystallized to yield 18.7 g of product 1K.

The mother liquor of 1K is crystallized to yield 6.3 g of product 1L.

1I, 1K and 1L is combined and recrystallized from $CHCl_3$/Heptane to yield 48 g.

The combined mother liquor of 1I, 1K, and 1L is concentrated to yield 31 g of 1M.

The product 1F provides the following data.

| Anal: 1F m.p. 229-230° C. | |
|---|---|
| Calc. | Found |
| C: 77.84 | 77.14 |
| H: 6.02 | 6.45 |
| N: 3.56 | 3.13 |

These data are consistent with the formula

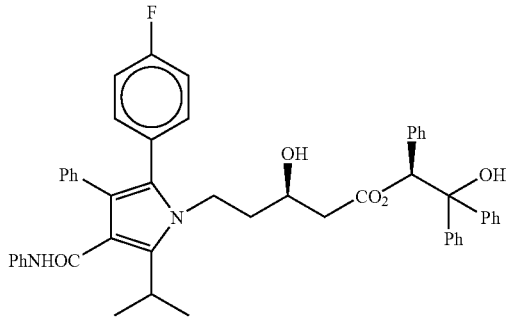

EXAMPLE 2

162 g (0.206M) of the combined products 1F, 1G, 1H and 1L of Example 1 are suspended in 800 ml Methanol/THF (5:3). Cooled to 0° C. and added to 11.7 g sodium methoxide. The mixture is stirred until everything is dissolved, then put in the freezer overnight. The reaction mixture is allowed to warm to room temperature, quenched with 15 ml HOAc, then concentrated in vacuo at 40° C. to obtain expected product as follows:

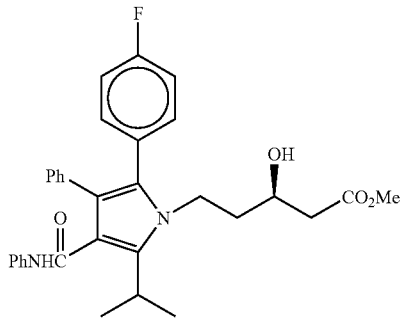

This product is added to 500 ml $H_2O$ and extracted twice with EtOAc (300 ml). The combined extracts are washed with saturated $NaHCO_3$, brine, dried over anhydrous magnesium sulfate, filtered and the solvent evaporated. The residue is chromatographed on silica gel in EtOAc/Heptane (1:4) as eluent to yield 109 g colorless oil which is recrystallized from $Et_2O$/Heptane to yield:

73.9 g first crop; white crystals 8.2 g second crop; white crystals.

The crystals provide the following data:

m.p. 125°–126° C., $\alpha_D^{20}$=4.23° (1.17M, $CH_3OH$)

| Calc. | Found |
|---|---|
| C: 72.76 | 72.51 |
| H: 6.30 | 6.23 |
| N: 5.30 | 5.06 |

These data are consistent with the formula

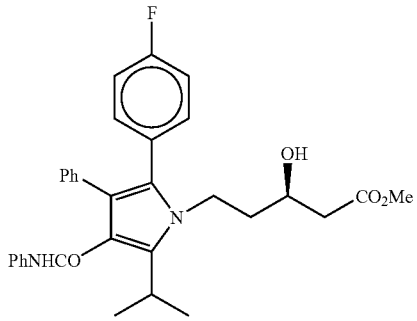

EXAMPLE 3

77 ml of diisopropylamine is dissolved in 250 ml THF in a 2000 ml three-neck flask equipped with thermometer and dropping funnel. The reaction mixture is kept under nitrogen. The mixture is cooled to −42° C. and added to 200 ml 2.2M of n-butyl lithium (in Hexane) dropwise over 20 minutes and stirred for 20 minutes before adding dropwise 62 ml of t-butylacetate, dissolved in 200 ml THF (over about 30 minutes). This mixture is stirred 30 minutes at −40° C., then 140 ml 2.2M of n-butyl lithium is added over 20 minutes. When addition is complete, 81 g of the product of Example 2 in 500 ml absolute THF is added as quickly as possible without allowing the temperature to rise above −40° C. Stirring is continued for four hours at −70° C. The reaction mixture is then quenched with 69 ml glacial acetic acid and allowed to warm to room temperature. The mixture is concentrated in vacuo and the residue is taken up in EtOAc, washed with water extensively, then saturated $NH_4Cl$, $NaHCO_3$ (saturated), and finally with brine. The organic layer is dried over anhydrous $MgSO_4$, filtered and the solvent evaporated. The NMR of the reaction is consistent with starting material plus product in about equal amounts plus some material on the baseline of the TLC. The material of the baseline of the TLC is separated from starting material and the product is extracted by acid/base extraction. The organic phase is dried and concentrated in vacuo to yield 73 g. The NMR and TLC are consistent with the formula

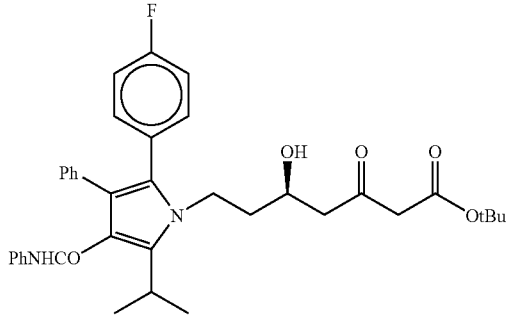

EXAMPLE 4

73 g crude product of Example 3 is dissolved in 500 ml absolute THF and 120 ml triethyl borane is added, followed by 0.7 t-butylcarboxylic acid. The mixture is stirred under a dry atmosphere for 10 minutes, cooled to −78° C. and 70 ml methanol is added and followed by 4.5 g sodium borohydride. The mixture is again stirred at −78° C. for six hours. Then poured slowly into a 4:1:1 mixture of ice/30% $H_2O_2$/$H_2O$. This mixture is stirred overnight then allowed to warm to room temperature.

$CHCl_3$ (400 ml) is added and the mixture is partitioned. The water layer is extracted again with $CHCl_3$. The organic extracts are combined and washed extensively with $H_2O$ until no peroxide could be found. The organic layer is dried over $MgSO_4$, filtered and the solvent is evaporated.

The residue is treated by flash chromatography on silica gel, i.e. EtOAc/Hexane 1:3 to yield 51 g.

The product is dissolved in THF/MeOH and added to 100 ml in NaOH, then stirred for four hours at room temperature. The solution is concentrated at room temperature to remove organic solvent, added to 100 ml $H_2O$, and extracted with $Et_2O$ twice. The aqueous layer is acidified with 1N HCl and extracted with EtOAc three times. The combined organic layers are washed with $H_2O$. The organic layer is dried with anhydrous $MgSO_4$, filtered, and the solvent evaporated. The residue is taken up in 2 liters of toluene and heated to reflux using a Dean-Stark trap for 10 minutes.

The reaction mixture is allowed to cool to room temperature overnight. Reflux is repeated for 10 minutes and cooled for 24 hours.

The procedure above is repeated. The reaction is left at room temperature for the next 10 days, then concentrated to yield 51 g of colorless foam.

This product is dissolved in minimum $CHCl_3$ and chromatographed on silica gel eluting with EtOAc/Heptane (50:50) to yield 23 g in pure material.

Chromatography on silica gel in $CHCl_3$/2-propanol (98.5:1.5) yields 13.2 g.

| Calc. |
|---|
| C: 73.31<br>H: 6.15<br>N: 5.18 |

EXAMPLE 5

Preparation of 2R-trans-5-(4-fluorophenyl)-2-(1-methylethyl)-N,4-diphenyl-1-[2-tetrahydro-4-hydroxy-6-oxo-2H-pyran-2-yl)ethyl]-1H/-pyrrole-3-carboxamide The product of Example 4 is recrystallized from EtOAc/Hexane. Fraction 1 yields 8.20 g of 4A. The another liquor yields 4.60 g of 4B, HPLC of 4B shows 100% of the product to be the [R-(R*R*)] isomer. 4A is recrystallized to yield 4.81 g of 4C. 4B is chromatographed on silica gel in $CHCl_3$/2-propanol to yield 4.18 g colorless foam of 4D showing $\alpha_D^{23}$+24.53° (0.53% in $CHCl_3$). 4C is recrystallized and the mother liquor of 4C is to yield 2.0 g.HPLC which indicates 100% of the R-trans isomer 2R-trans-5-(4-fluorophenyl)-2-(1-methylethyl)-N,4-diphenyl-1-[2-tetrahydro-4-hydroxy-6-oxo-2H-pyran-2-yl)ethyl]-1H-pyrrole-3-carboxamide.

EXAMPLE 6

Preparation of diastereomeric α-methylbenzylamides

A solution of the racemate, trans-(±)-5-(4-fluorophenyl)-2-(1-methylethyl)-N,4-diphenyl-1-[2-tetrahydro-4-hydroxy-6-oxo-2H-pyran-2-yl)ethyl]-1H-pyrrole-3-carboxamide, (30 g, 55.5 ml) in (R)-(+)-α-methylbenzylamine (575 ml, 4.45 mol, 98% Aldrich) is stirred overnight at room temperature.

The resulting solution is then diluted with ether (2 l) and then washed exhaustively with 2M HCl (4×500 ml), water (2×500 ml) and brine (2×500 ml). The organic extract is then dried over $MgSO_4$, filtered and concentrated in vacuo to yield 28.2 g of the diastereomeric α-methylbenzylamides as a white solid; m.p. 174.0°–177°. The α-methylbenzylamides are separated by dissolving 1.5 g of the mixture in 1.5 ml of 98:1.9:0.1 $CHCl_3$:$CH_3OH$:$NH_4OH$ (1000 mg/ml) and injecting onto a preparative HPLC column (silica gel, 300 mm×41.4 mm I.D.) by gastight syringe and eluting with the above solvent mixture. Fractions are collected by UV monitor. Diastereomer 1 elutes at 41 minutes. Diastereomer 2 elutes at 49 minutes. Center cut fractions are collected. This procedure is repeated three times and the like fractions are combined and concentrated. Examination of each by analytical HPLC indicates that diastereomer 1 is 99.84% pure and diastereomer 2 is 96.53% pure. Each isomer is taken on separately to following Examples.

EXAMPLE 7

Preparation of 2R-trans-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide To an ethanolic solution (50M) of diastereomer 1 of Example 6, [3R-[3R*(R*),5R*]]-2-(4-fluorophenyl)-[β],[δ]-dihydroxy-5-(1-methylethyl)-3-phenyl-4-[(phenylamino)carbonyl]-N-(1-phenylethyl-1H-pyrrole-1-heptanamide, (hydroxy centers are both R) (1 g, 1.5 mmol) is added 1N NaOH (3.0 ml, 3 mmol). The resulting solution is heated to reflux for 48 hours.

The solution is cooled to room temperature and concentrated in vacuo. The residue is resuspended in water and carefully acidified with 6N HCl. The resulting acidic solution is extracted with ethyl acetate. The organic extract is washed with water, brine, dried over $MgSO_4$, filtered and concentrated in vacuo. This residue is redissolved in toluene (100 ml) and heated to reflux with azeotropic removal of water for three hours. This is cooled to room temperature and concentrated in vacuo to yield 1.2 g of a yellow semi-solid. Flash chromatography on silica gel eluting with 40% EtOAc/Hexane gives 0.42 g of a white solid which still contains impurities. This is rechromatographed to give 0.1 g of essentially pure R,R, enantiomer, 2R-trans-5-(4-fluorophenyl)-2-(1-methylethyl)-N,4-diphenyl-1-[2-tetrahydro-4-hydroxy-6-oxo-2H-pyran-2-yl)ethyl]-1H-pyrrole-3-carboxamide, as a white foam. HPLC shows this material to be 94.6% chemically pure $[\alpha]_D^{23}$:0.51% in $CHCl_3$=25.5°. The peak at room temperature=53.46 minutes is tentatively assigned to an unknown diastereomer resulting from the 2% (S)-(−)-α-methylbenzylamine present in the Aldrich α-methylbenzylamine.

EXAMPLE 8

Preparation of 2S-trans-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide-(S,S enantiomer of the compound prepared in Example 5

Carrying out the procedure described in Example 7 on diastereomer 2 afforded 0.6 g of a foamy solid which was flash chromatographed on silica gel. Elution with 50% EtOAc/Hexane gave 0.46 g of essentially pure S,S, enantiomer 2S-trans-5-(4-fluorophenyl)-2-(1-methylethyl)-N,4-diphenyl-1-[2-(tetrahydro-4-hydroxy-6-oxo-2H-pyran-2-yl) ethyl]-1H-pyrrole-3-carboxamide, as a white foam. HPLC showed this material to be 97.83% chemically pure. $[\alpha]_D^{23}$= 0.51% in $CHCl_3$=−24.8%.

EXAMPLE 9

Hydrolysis of chemical lactone of formula II

To a room temperature, solution of the lactone in THF is added a solution of sodium hydroxide in water. The mixture is stirred for two hours HPLC:99.6% (product); 0.34 to (starting lactone). The mixture is diluted with 3 L water, extracted with ethyl acetate (2×1 L) and acidified to pH×4 by addition of 37 ml of 5N hydrochloric acid. The aqueous layer is extracted with 2×1.5 L portions of ethyl acetate. The combined ethyl acetate extracts are washed with 2×1 L of water, brine and dried, gave after filtration the ethyl acetate solution of the required face-acid. This solution is used directly in the fraction of the N-methylglucamine salt.

The ethyl acetate extracts from the brine-water were concentrated to give 15.5 g of an off-white solid.

EXAMPLE 10

Calcium Salt from Sodium Salt and/or Lactone

Dissolve one mole lactone (540.6 g) in 5 L of MeOH; after dissolution add 1 L $H_2O$. While stirring, add one equivalent NaOH and follow by HPLC until 2% or less lactone and methyl ester of the diolacid remains (cannot use an excess of NaOH, because $Ca(OH)_2$ will form an addition of $CaCl_2$). Charge NaOH as caustic (51.3 ml, 98 eq.) or as pellets (39.1 g, 0.98 eq.).

The above procedure is shown as follows:

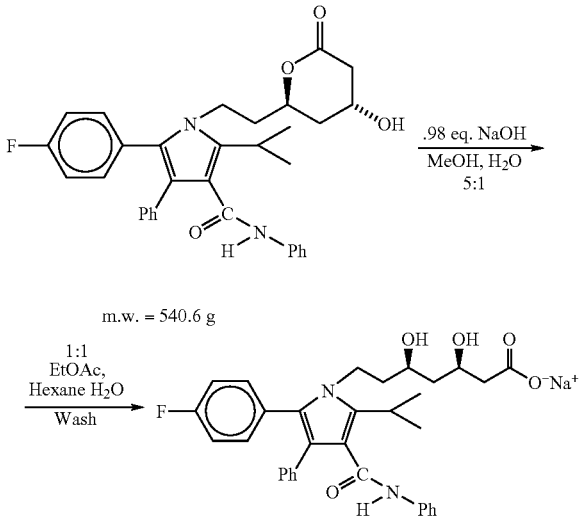

Upon completion of hydrolysis, add 10 L $H_2O$, then wash at least two times with a 1:1 mixture of EtOAc/Hexane. Each wash should contain 10 L each of EtOAc/Hexane. If sodium salt is pure, add 15 L of MeOH. If it is impure and/or contains color, add 100 g of G-60 charcoal, stir for two hours and filter over supercel. Wash with 15 L MeOH. Perform a wt/vol % on the reaction mixture, by HPLC, to determine the exact amount of salt in solution.

Dissolve 1 eq. or slight excess $CaCl_2.2H_2O$ (73.5 g) in 20 L $H_2O$. Heat both reaction mixture and $CaCl_2$ solution to 60° C. Add $CaCl_2$ solution slowly, with high agitation. After completion addition, cool slowly to 15° C. and filter. Wash filter cake with 5 L $H_2O$. Dry at 50° C. in vacuum oven.

Can be recrystallized by dissolving in 4 L of EtOAc (50° C.) filtering over supercel, washing with 1 L EtOAc, then charging 3 L of hexane to the 50° C. rxn solution.

The above procedure is shown as follows:

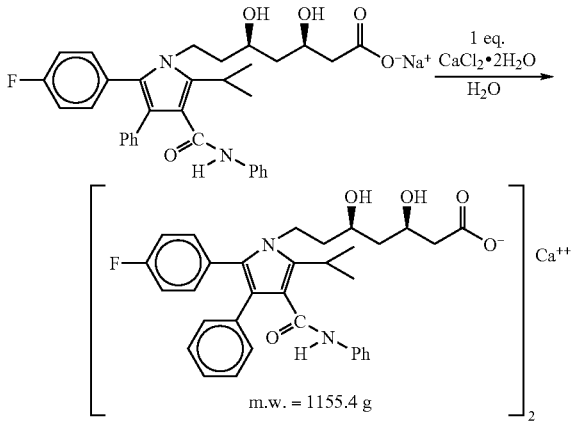

EXAMPLE 11

Treatment of Ethyl Acetate Solution of Free-acid of the Formula I with N-methylglucamine To a solution of the free-acid of the formula I (0.106M) in ethyl acetate (3 L) is added a solution of N-methylglucamine (20.3 g, 0.106 m) in (1:1) water-acetone (120 ml, 120 ml) with vigorous stirring at room temperature. Stirring is continued for 16 hours and the hazy solution concentrated in vacuo to ~250 mp. Toluene (1 L) is added and the mixture concentrated to a white solid ~100 g. The solid is dissolved in 1670 ml acetone and filtered into a three-neck flask equipped with a mechanical stirrer and thermostat controlled thermometer. The flask and filter is washed with 115 ml (1:1) water-acetone and the clear solution is cooled slowly. This provided a precipitate which is re-dissolved by heating back to 65° C. Addition of a further 20 ml of water followed by the washing gives a crystalline product which was isolated by filtration. The solids are washed with 1200 ml $CH_3Cl$ and vacuum dried at 255° to give a white solid. Analysis of this material indicates that it contains 4% amine as well as 0.4% residual acetone and 0.67% water. Analytical results are noted as follows:

Melting point: 105°–155° C. (decomposition) Analysis Expected: C=63.73; H-6.95; N=5.57; F2=9.53. Analysis Found: C=62.10; H-6.89; N-5.34; F2. C=61.92; H-7.02; N=5.38; F2.

$H_2O$=0.47% (KF)

HPLC: MeOH, $H_2O$, THF (40; 550; 250)

Econosil: C18, 5 μ, 25 CM 256 nm: 1.0 ml/min.

6–81 min.: 98.76%

Opt. Ret.: $[\alpha]\cdot b$=−10.33° (c=1.00, MeOH)

Residual Solvents: $CH_2CH$=0.26%

Titrations:

$HClO_4$ (0.1N)=203.8%

$Bu_4NOH$ (0.1N)=98.5%

Other salts prepared in a manner analogous to those processes appropriately selected from Examples 10 and 11 above may be the potassium salt, hemimagnesium salt, hemizinc salt or the 1-deoxy-2-(methylamino)-D-glucitol complex of the compound of formula I.

I claim:

[1. [R-(R*,R*)]-2-(4-fluorophenyl)-β,δ-dihydroxy-5-(1-methylethyl)-3-phenyl-4-[(phenylamino)-carbonyl]-1H-pyrrole-1-heptanoic acid or (2R-trans)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide; or pharmaceutically acceptable salts thereof.]

[2. A compound of claim 1 which is [R-(R*R*)]-2-(4-fluorophenyl)-β,δ-dihydroxy-5-(1-methylethyl)-3-phenyl-4-[(phenylamino)carbonyl]-1H-pyrrole-1-heptanoic acid.]

[3. A compound of claim 1 which is (2R-trans)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide.]

[4. The monosodium salt of the compound of claim 2.]

[5. The monopotassium salt of the compound of claim 2.]

6. The hemicalcium salt of [the compound of claim 2] *[R-(R*,R*)]-2-(4-fluorophenyl)-β,δ-dihydroxy-5-(1-methylethyl)-3-phenyl-4-[(phenylamino)-carbonyl]-1H-pyrrole-1-heptanoic acid.*

[7. The N-methylglucamine salt of the compound of claim 2.]

[8. The hemimagnesium salt of the compound of claim 2.]

[9. The hemizinc salt of the compound of claim 2.]

[10. The 1-deoxy-1-(methylamino)-D-glucitol mixture with the compound of claim 2.]

[11. A pharmaceutical composition for treating hypercholesterolemia comprising a hypocholesterolemic effective amount of a compound of claim 1 and a pharmaceutically acceptable carrier.]

[12. A method of inhibiting cholesterol synthesis in a human suffering from hypercholesterolemia comprising administering a compound of claim 1 in unit dosage form.]

*13. A pharmaceutical composition for treating hypercholesterolemia comprising a hypocholesterolemic effective amount of the hemicalcium salt of [R-(R*,R*)]-2-(4-fluorophenyl)-β,δ-dihydroxy-5-(1-methylethyl)-3-phenyl-4-[(phenylamino)-carbonyl]-1H-pyrrole-1-heptanoic acid and a pharmaceutically acceptable carrier.*

*14. A method of inhibiting cholesterol synthesis in a human suffering from hypercholesterolemia comprising administering to said human the hemicalcium salt of [R-(R*,R*)]-2-(4-fluorophenyl)-β,δ-dihydroxy-5-(1-methylethyl)-3-phenyl-4-[(phenylamino)-carbonyl]-1H-pyrrole-1-heptanoic acid in unit dosage form.*

* * * * *

UNITED STATES PATENT AND TRADEMARK OFFICE

CERTIFICATE OF CORRECTION

PATENT NO. : RE 40,667 E
APPLICATION NO. : 11/653830
DATED : March 17, 2009
INVENTOR(S) : Bruce D. Roth It is certified that error appears in the above-identified patent and that said Letters Patent is hereby corrected as shown below:

Title page, item 56 in the section entitled "Other Publications," please add the following references:

--Warner-Lambert/Parke-Davis Pharmaceutical Research Report No. RR967-01212, PD 123832 (Anti-Atherosclerosis) – Preformulation Summary, identified as DTX 28 in *Pfizer, Inc et al. v. Ranbaxy Laboratories Limited, et al.*, US District Court, District of Delaware, 03-209-JJF.

Warner-Lambert Report, "Atherosclerosis Drug Discovery Team Report," December 12, 1989, referred to at paragraph 351 of *Ranbaxy Australia Pty Ltd v. Warner-Lambert Company LCC (No. 2)*, [2006] FCA 1787.

Warner-Lambert internal report dated December 15, 1987, summarizing results of CSI 107, referred to at paragraph 291 of *Ranbaxy Australia Pty Ltd v. Warner-Lambert Company LCC (No. 2)*, [2006] FCA 1787.

Warner-Lambert internal memorandum dated December 5, 1989, referred to at paragraph 341 of *Ranbaxy Australia Pty Ltd v. Warner-Lambert Company LCC (No. 2)*, [2006] FCA 1787.

Forms IV. Lists for Atorvastatin Calcium in Canada.

US Orange Book entries for atorvastatin.--

Signed and Sealed this

Fifth Day of May, 2009

John Doll

JOHN DOLL
*Acting Director of the United States Patent and Trademark Office*

Disclaimer

RE.40,667 E — Bruce Roth, San Jose, CA (US). [R-(R*R*)]-2-(4-FLUOROPHENYL)- β,δ-DIHYDROXY-5-(1-METHYLETHYL-3-PHENYL-4-[(PHENYLAMINO)CARBONYL]-1H-PYRROLE-1-HEPTANOIC ACID, ITS LACTONE FORM AND SALTS THEREOF. Patent dated March 17, 2009. Disclaimer filed July 8, 2010, by the assignee, Warner-Lambert Company LLC.

The term of this patent shall not extend beyond the expiration date of Patent No. 5,273,995.

*(Official Gazette, August 17, 2010)*